(12) United States Patent
Berlin et al.

(10) Patent No.: US 6,586,460 B1
(45) Date of Patent: Jul. 1, 2003

(54) HETEROAROTINOIDS CONTAINING UREA OR THIOUREA LINKER

(75) Inventors: Kenneth Darrell Berlin, Stillwater, OK (US); Doris M. Benbrook, Oklahoma City, OK (US); Eldon C. Nelson, Stillwater, OK (US)

(73) Assignees: The Board of Regents for Oklahoma State University, Stillwater, OK (US); The Board of Regents for University of Oklahoma, Norman, OK (US)

( * ) Notice: Subject to any disclaimer, the term of this patent is extended or adjusted under 35 U.S.C. 154(b) by 0 days.

(21) Appl. No.: 09/824,547

(22) Filed: Apr. 2, 2001

(51) Int. Cl.7 ...................... C07D 335/04; A61K 31/38; A61P 35/00
(52) U.S. Cl. .......................... 514/432; 514/456; 549/23; 549/404
(58) Field of Search ................... 549/23, 404; 514/432, 514/456

(56) References Cited

U.S. PATENT DOCUMENTS

| | | | |
|---|---|---|---|
| 4,826,984 A | * 5/1989 | Berlin et al. | 546/134 |
| 4,833,254 A | 5/1989 | Berlin et al. | 405/10 |
| 4,975,455 A | 12/1990 | Brion et al. | 31/35 |
| 4,977,276 A | * 12/1990 | Berlin et al. | 549/58 |
| 4,985,448 A | * 1/1991 | Zilch et al. | 548/411 |
| 5,006,550 A | 4/1991 | Chandraratna | 31/35 |
| 5,252,342 A | 10/1993 | Howell et al. | 33/24 |
| 5,373,019 A | * 12/1994 | Zilch et al. | 514/423 |
| 6,054,467 A | 4/2000 | Gjerset | 43/42 |
| 6,110,960 A | 8/2000 | Janusz et al. | 31/38 |
| 6,121,245 A | 9/2000 | Firshein | 31/70 |
| 6,121,263 A | 9/2000 | Brown | 31/53 |

FOREIGN PATENT DOCUMENTS

| | | | |
|---|---|---|---|
| EP | 0 130 795 A2 | 1/1985 | C07D/311/58 |
| EP | 0 350 846 A2 | 1/1990 | C07D/311/58 |
| EP | 0 405 028 A1 | 1/1991 | C07D/335/06 |
| FR | 2 390 428 | 8/1978 | C07C/175/00 |
| GB | 2 119 801 A | 11/1983 | C07D/215/02 |
| WO | WO 85/00806 | 2/1985 | C07C/69/78 |
| WO | WO 98/07716 | 2/1998 | C07D/311/58 |

OTHER PUBLICATIONS

Brown et al. Med. Chem. (1990), 33 (6), 1771–81.*
K. D. Berlin. Biologically Active Heteroarotinoids Exhibiting Anticancer Activity and Decreased Toxicity. *Journal of Medicinal Chemistry*; 1997, 40(22); 3567–3583.
K. D. Berlin. Synthesis and Characterization of Heteroarotinoids Demostrate structure Specificity Relationships. *Journal of Medicinal Chemistry*; 1998, 41(19); 3753–3757.
A. Dhar, S. Liu, J. Klucik, K. D. Berlin, M. M. Madler, S. Lu, R. T. Ivey, D. Zacheis, C. W. Brown, E. C. Nelson, P. J. Birckbichler, and D. M. Benbrook. Synthesis, Structure–Activity Relationships, and RARγ–Ligand Interactions of Nitrogen Heteroarotinoids. *Journal of Medicinal Chemistry*; 1999, 42(18); 3602–3614.
H. Kagechika, E. Kawachi, Y. Hashimoto, T. Himi and K. Shudo. "Rebinobenzoic Acids. 1. Structure—Activity Relationships of Aromatic Amides with Retinoidal Activity". *Journal of Medicinal Chemistry*; vol. 31, 1988; 2182–2192.
U. Pastorino, R. P. Warrell, Jr., F. Formelli. "Clinical Pharmacology of the Retinoids". *Retinoids in Oncology*, 1995, pp. 55–64.
L. W. Spruce, S. N. Rajadhyasksha, K. D. Berlin, J. B Gale, E. T. Miranda, W. T. Ford, E. C. Blossey, A. K. Verma, M. B. Hossain, D. van der Helm, and T. R. Breitman. "Heteroarotinoids. Synthesis, Characterization, and Biological Activity in Terms of an Assessment of these Systems to Inhibit the Induction of Ornithine Decarboxylase Activity and to Induce Terminal Differentiation of HL–60 Cells". *Journal of Medicinal Chemistry*; 1987, 30; 1174–1480.
L. W. Spruce, J. B. Gale, K. D. Berlin, A. K. Verma, T. R. Breitman, X. Ji, and D. van der Helm. "Novel Heteroarotinoids: Symthesis and Biological Activity". *Journal of Medicinal Chemistry*; 1991, 34; 430–439.
K. M. Waugh, K. D. Berlin, W. T. Ford, E. M. Holt, J. P. Carrol, P. R. Schomber, and L. J. Schiff. "Synthesis and Characterization of Selected Heteroarotinoids—Pharmacological Activity as Assessed in Vitamin A Deficient Hamster Tracheal Organ Cultures—Single Crystal X–ray Diffraction Analysis of 4,4–Dimethylthiochrom–6–yl Methyl Ketone–1,1–Dioxide and Ethyl (E)–p–[2–(4, 4–Dimethylthiochroma–6–yl)propenyl]benzoate". *Journal of Medicinal Chemistry*; 1985, 28; 116–124.
W. J. Welsh, V. Cody, K. Suwinska, K. D. Berlin, S. N. Radjadhyaksha, S. Subramanian, and A. K. Verma. "Heteroarotinoids; Crystal and Molecular Structure Analysis of Methyl (Z)– and Methyl (E)–4–[2–(4, 4–Dimethylthiochroman–6–yl)–1–propenyl]benzoate". *Structural Chemistry*; 1991–2; 515–522.
D. Zacheis, A. Dhar, S. Lu, M. M. Madler, J. Klucik, C. W. Brown, S. Liu, F. Clement, S. Subramanian, G. M. Weerasekare, K. D. Berlin, M. A. Gold, J. R. Houck, Jr., K. R. Fountain, and D. M. Benbrook. Heteroarotinoids Inhibit Head and Neck Cancer Cell Lines in Vitro and in Vivo Through Both RAR and RXR Retinoic Acid Receptors. *Journal of Medicinal Chemistry*; 1999, 42(21); 4434–4445.

* cited by examiner

Primary Examiner—Joseph K. McKane
Assistant Examiner—Kamal Saeed
(74) Attorney, Agent, or Firm—Fellers, Snider, Blankenship, Bailey & Tippens, P.C.

(57) ABSTRACT

Compounds, known as heteroarotinoids, having varying abilities to inhibit growth of certain cancerous cells, induce normal cell differentiation, and induce apoptosis or death of cancerous cells, of the general formula:

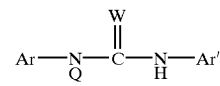

in which:

Ar and Ar' denote aryl substituents, and wherein at least one of said aryl substituents comprises an aromatic ring having at least one heteroatom in a fused, partially saturated ring;

W denotes O or S; and

Q denotes H or i-$C_3H_7$.

27 Claims, 2 Drawing Sheets

HETEROAROTINOIDS CONTAINING UREA OR THIOUREA LINKER

STATEMENT REGARDING FEDERALLY SPONSORED RESEARCH

The Government of the United States of America has certain rights in this invention pursuant to Grant No. 5 R01 CA73639-03 awarded by the National Institutes of Health and/or Grant No. 5 R01 CA77711-03 awarded by the National Cancer Institute.

BACKGROUND OF INVENTION

1. Field of the Invention

This invention relates to anticancer compositions in terms of the inhibition of growth of certain cancerous cell lines and in terms of apoptosis or programmed (or induced) cancer cell death. Specifically, the invention relates to certain heteroarotinoids and derivatives thereof.

2. Background

Retinoids (vitamin A and derivatives thereof) is a name associated with a family of compounds both of natural and synthetic origin. There is significant interest in such molecules because of the observed strong anticancer activity in a number of assays including the hamster tracheal organ culture (TOC) assay, the omithine decarboxylase (ODC) assay, and with HL-60 cells (human leukemic cell line). Heteroarotinoids are a group of derivatives that contain an aromatic ring and at least one heteroatom in a fused, partially saturated ring bonded to an aromatic ring.

Examples of heteroarotinoids and the activity of such in the assays cited above are found in several papers such as: *Journal of Medicinal Chemistry*, 1985, Vol. 28, pages 116–124, entitled "Synthesis and Characterization of Selected Heteroarotinoids—Pharmacological Activity as Assessed in Vitamin A Deficient Hamster Tracheal Organ Cultures—Single Crystal X-ray Diffraction Analysis of 4,4-Dimethylthiochrom-6-yl Methyl Ketone-1,1-Dioxide and Ethyl (E)-p-[2-(4,4-Dimethylthiochroma-6-yl)propenyl] benzoate", by K. M. Waugh, K. D. Berlin, W. T. Ford, E. M. Holt, J. P. Carrol, P. R. Schomber, and L. J. Schiff; *Journal of Medicinal Chemistry*, 1987, Vol. 30, pages 1174–1480, entitled "Heteroarotinoids. Synthesis, Characterization, and Biological Activity in Terms of an Assessment of these Systems to Inhibit the Induction of Ornithine Decarboxylase Activity and to Induce Terminal Differentiation of HL-60 cells", by L. W. Spruce, S. N. Rajadhyaksha, K. D. Berlin, J. B Gale, E. T. Miranda, W. T. Ford, E. C. Blossey, A. K. Verma, M. B. Hossain, D. van der Helm, and T. R. Breitman; and *Journal of Medicinal Chemistry*, 1991, Vol. 34, pages 430–439, entitled "Novel Heteroarotinoids: Synthesis and Biological Activity", by L. W. Spruce, J. B. Gale, K. D. Berlin, A. K. Verma, T. R. Breitman, X. Ji, and D. van der Helm.

Another report entitled "Heteroarotinoids; Crystal and Molecular Structure Analysis of Methyl (z)- and Methyl (E)-4-[2-(4,4-Dimethylthiochroman-6-yl)-1-propenyl] benzoate", in the journal entitled *Structural Chemistry*, 1991, Vol. 2, pages 515–522, by W. J. Welsh, V. Cody, K. Suwinska, K. D. Berlin, S. N. Radjadhyaksha, S. Subramanian, and A. K. Verma, contains background data pertinent to the invention as well. Other background information on heteroarotinoids is found in U.S. Pat. No. 4,826,984 (May 2, 1989), U.S. Pat. No. 4,883,254 (May 23, 1989) and U.S. Pat. No. 4,997,276 (Dec. 11, 1990). Summaries of the biochemistry, chemistry, and prior biological activity of retinoids, including the few heteroarotinoids known, are found in five treatises, namely "*Chemistry and Biology of Synthetic Retiniods*", by M. I. Dawson and W. H. Okamura, editors, CRC Press: Boca Raton, Fla., 1990, "*The Retinoids*", Volumes I and II, by M. B. Sporn, A. B. Roberts, and D. S. Goodman, editors, Academic Press: Orlando, Fla., 1984, "*The Retinoids*", 2$^{nd}$ Edition, by M. B. Sporn, A. B. Roberts, and D. S. Goodman, editors, Raven Press: New York, N.Y., 1994, and "*Retinoids*", Fifth Edition, Vol. 3, by M. I. Dawson, Chp 44, in *Burger's Medicinal Chemistry and Drug Discovery*, M. E. Wolff, editor, J. Wiley and Sons, Inc., New York, 1996.

More recent work in the general area includes: *Journal of Medicinal Chemistry*, 1999, Vol. 42, pages 3602–3614 entitled "Synthesis, Structure-Activity Relationships, and RARγ-Ligand Interactions of Nitrogen Heteroarotinoids" by A. Dhar, S. Liu, J. Klucik, K. D. Berlin, M. M. Madler, S. Lu, R. T. Ivey, D. Zacheis, C. W. Brown, E. C. Nelson, P. J. Birckbichler, and D. M. Benbrook and *Journal of Medicinal Chemistry*, 1999, Vol. 42, pages 4434–4445, entitled "Heteroarotinoids Inhibit Head and Neck Cancer Cell Lines in vitro and in vivo Through Both RAR and RXR Retinoic Acid Receptors" by D. Zacheis, A. Dhar, S. Lu, M. M. Madler, J. Klucik, C. W. Brown, S. Liu, F. Clement, S. Subramanian, G. M. Weerasekare, K. D. Berlin, M. A. Gold, J. R. Houch, Jr., K. R. Fountain, and D. M. Benbrook.

The heteroarotinoids described and claimed herein have not been, to the knowledge of the inventors, previously described in either the patent or literature art. As will be seen, the inventive heteroarotinoids significantly differ both in structure and activity as compared to known compounds. No assertion is made that the inventive heteroarotinoids activate the common retinoid receptors.

SUMMARY OF THE INVENTION

The present invention involves the synthesis and use of certain unusual heteroarotinoids which have varying abilities to inhibit growth of certain cancerous cells, induce normal cell differentiation, and induce apoptosis or death of cancerous cells. The inventive structures consist of a three atom urea or thiourea linker group with aryl substituents, one on each end of the group and bonded to each of the nitrogen atoms. One of the aryl substituents has at least one heteroatom in a fused, partially saturated ring. Thus, the inventive heteroarotinoids have in common the basic molecular unit shown below, wherein each aryl substituent is denoted Ar and W and Q denote the indicated alternatives:

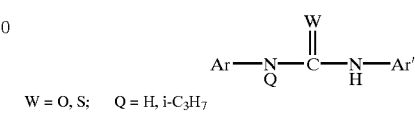

W = O, S;   Q = H, i-C$_3$H$_7$

The inventive heteroarotinoids appear to be much less toxic than endogenous and synthetic retinoid standards, e.g. trans-retinoic acid, 9-cis-retinoic acid, 13-cis-retinoic acid, etretinate, acitretin, and 4-HPR, on the basis of gross examination in tissue cultures and in animal models. Moreover, the unique three-atom linkage endows the inventive molecules with a certain rigidity not possessed in heteroarotinoids having a conventional two-carbon ester linker group. This structural feature is reasoned to be important in the interaction of the molecules with nuclear receptors and is believed to contribute to decreased toxicity insofar as the body is well adept at processing urea derivatives.

The heteroarotinoids of the present invention are very peripherally related in structure to trans-retinoic acid, 9-cis-retinoic acid, and 13-cis-retinoic acid as illustrated. The inventive heteroarotinoids, shown in the general structures 1 and 2, have either oxygen or sulfur as the heteroatom, two aryl rings depending from the three atom linker (either urea or thiourea), and possess the indicated alternatives at G, R, X, Y and Z:

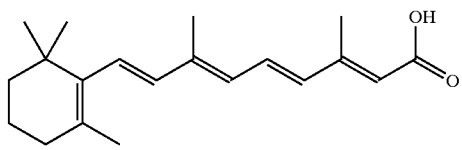

trans-retinoic acid
[t-RA]

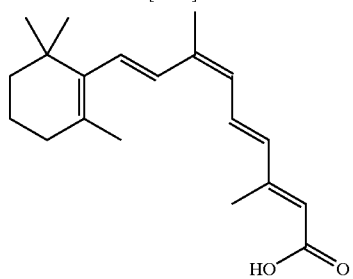

9-cis-retinoic acid
[9-c-RA]

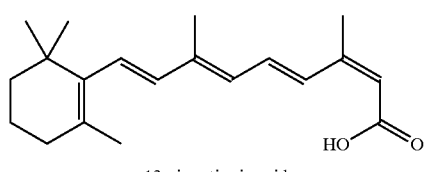

13-cis-retinoic acid
[13-c-RA]

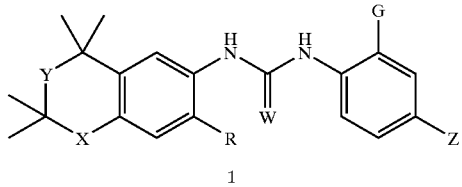

1

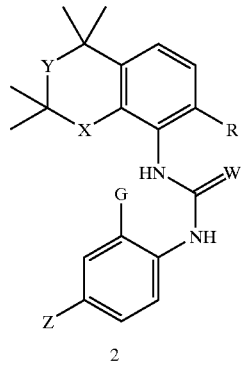

2

G = H, CH₃,
R = H, CH₃, OCH₃
W = O, S
X = CH₂, O, S
Y = CH₂, O, S
Z = CO₂H, CO₂alkyl (CH₃, C₂H₅, n-C₃H₇, i-C₃H₇), NO₂, SO₂NH₂

More particularly, the present invention encompasses heteroarotinoids of the following formulas, wherein G, R, Q, W and Z denote the indicated alternatives:

Isomeric heteroarotinoids having the formulas:

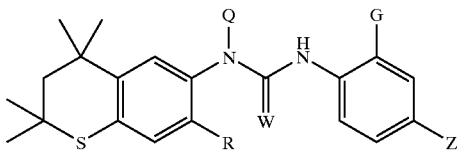

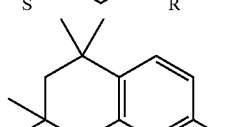

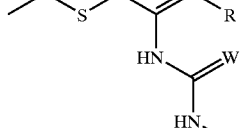

G = H, CH₃
R = H, CH₃, OCH₃
Q = H, i-C₃H₇
W = O, S
Z = NO₂, CO₂Et, CO₂-n-C₄H₉, SO₂NH₂

Isomeric heteroarotinoids having the formulas:

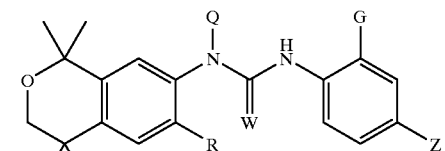

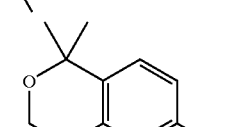

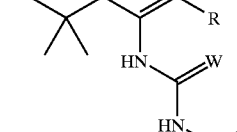

G = H, CH₃
R = H, CH₃, OCH₃
Q = H, i-C₃H₇
W = O, S
Z = NO₂, CO₂Et, CO₂-n-C₄H₉, SO₂NH₂

Heteroarotinoids with only one geminal group of the formulas:

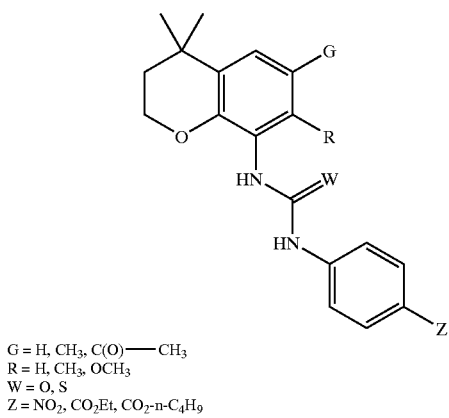

G = H, CH$_3$, C(O)—CH$_3$
R = H, CH$_3$, OCH$_3$
W = O, S
Z = NO$_2$, CO$_2$Et, CO$_2$-n-C$_4$H$_9$

Biological data generated from a large number of representative heteroarotinoids demonstrates significant inhibition of growth of three ovarian cancer cell lines, namely, Caov-3, SKOV-3, and OVCAR-3 cell lines. In addition, the inventive heteroarotinoids were tested against three cell lines of the cervix, namely, SiHa, HT-3, and C-33A, and one vulvar cell line, SW962, using t-RA, 9-c-RA and 4-HPR as controls, wherein a range of inhibitory prowess was observed with several of the heteroarotinoids outperforming the standards. Representative agents screened for apoptosis effect were as good or better than 9-c-RA in inducing apoptosis (cell death) of cancerous cells and were superior to 4-HPR, the clinically used agent. Xenograph investigations of representative heteroarotinoids using nude and immunocompromised mice injected with OVCAR-3 human carcinogenic cells were very demonstrative of the ability to reduce tumor volume and were comparable with that observed with 4-HPR. The concentrations used of the heteroarotinoids were in the microgram range. That the effect could be manifested at such a low concentration is suggestive of a low toxicity in mammals.

The heteroarotinoids according to the present invention hence find a use in therapy as antitumor agents, for the treatment or prophylaxis of benign, malignant, or metastatic neoplasms, as well as in the traditional indications for retinoids, such as skin disorders (acne, psoriasis), as well as degenerative disorders and/or inflammation of the mucosae.

The inventive heteroarotinoids may be readily provided in pharmaceutical compositions containing one or more of the heteroarotinoids, or of their addition salts with a pharmaceutically acceptable base or acid when a salifiable group is present, alone or in combination with one or more pharmaceutically acceptable, non-toxic, inert vehicles or excipients. Among such pharmaceutical compositions, there may be mentioned, more especially, those which are suitable for oral, parenteral, nasal, rectal, perlingual, ocular or respiratory administration, and in particular, tablets, simple or sugar-coated, sublingual tablets, sachets, packs, hard gelatin capsules, preparations to be dissolved under the tongue, bars, suppositories, creams, ointments, skin gels, injectable preparations or preparations to be swallowed, aerosols, eye or nose drops, and the like.

The appropriate dosage will vary according to an individual's age and weight, the administration route and the nature of the therapeutic indication and of any associated treatments, but will be an amount effective to exert a therapeutic effect on a tumor by any mechanism such as by killing tumor cells, reducing cell proliferation or reducing the size of the tumor or, in the case of its use as a chemoprevention agent, an amount sufficient to exert a prophylactic effect or a preventative effect on recurrence after primary therapy, or a prevention of secondary tumors.

In another aspect of the invention, the inventive molecules may also find use as a sensitizing agent administered in advance of or conconcurrently with a chemotherapeutic agent to increase the selectivity and/or efficacy of the chemotherapeutic agent. In this respect an effective amount refers to amounts of the inventive heteroarotinoids capable of sensitizing tumor cells to treatment by one or more chemotherapy agents, including cisplatin, carboplatin, VP 16, teniposide, daunorubicin, doxorubicin, dactinomycin, mitomycin, plicamycin, bleomycin, procarbazine, nitrosourea, cyclophosphamide, bisulfan, melphalan, chlorambucil, ifosfamide, merchlorehtamine, taxol, taxotere, anthracyclines, and ionizing radiation.

A better understanding of the present invention, its several aspects, and its advantages will become apparent to those skilled in the art from the following detailed description, taken in conjunction with the attached drawings, wherein there is shown and described the preferred embodiment of the invention, simply by way of illustration of the best mode contemplated for carrying out the invention.

DETAILED DESCRIPTION OF THE PREFERRED EMBODIMENT

Figure 1:
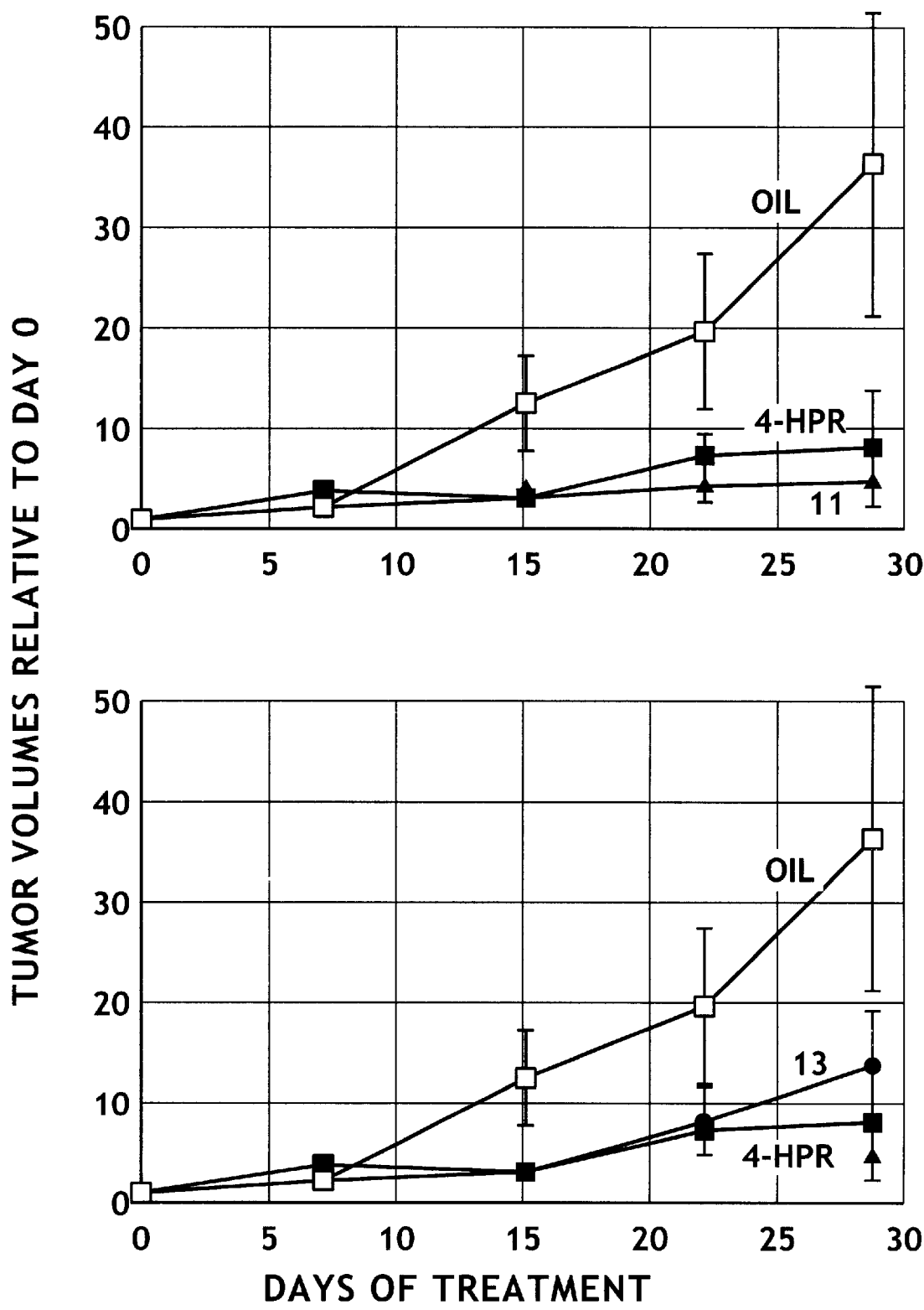
FIG. 1 is a comparative summary of average tumor volume over time as measured in mice in connection with in vivo tumor xenographs conducted to evaluate the inventive heteroarotinoids.

Before explaining the present invention in detail, it is important to understand that the invention is not limited in its application to the details of the embodiments and steps described herein. The invention is capable of other embodiments and of being practiced or carried out in a variety of ways. It is to be understood that the phraseology and terminology employed herein is for the purpose of description and not of limitation.

Representative examples of the benzothiopyran derivatives of formulas 1 and 2 and of the preferred reaction mechanisms used to obtain these compounds are illustrated in the reaction schemes below. As the first step, the synthesis of a few sulfur-containing members of 1 is outlined. Conversion of known structure 3 via nitration gave both the 6-isomer 4 and the 8-isomer 5, which were separated by solvent extraction and purified by recrystallization. Purified 4 and 5 were individually reduced to the corresponding amines 6 and 7, respectively, as in SCHEME I. In a similar reaction sequence, the 7-methyl derivative 8 was converted to the corresponding 6-nitro analog 9 which, in turn, was reduced to the amine 10 in Scheme II.

SCHEME I

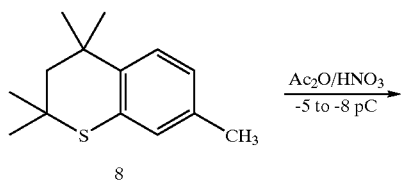

SCHEME II

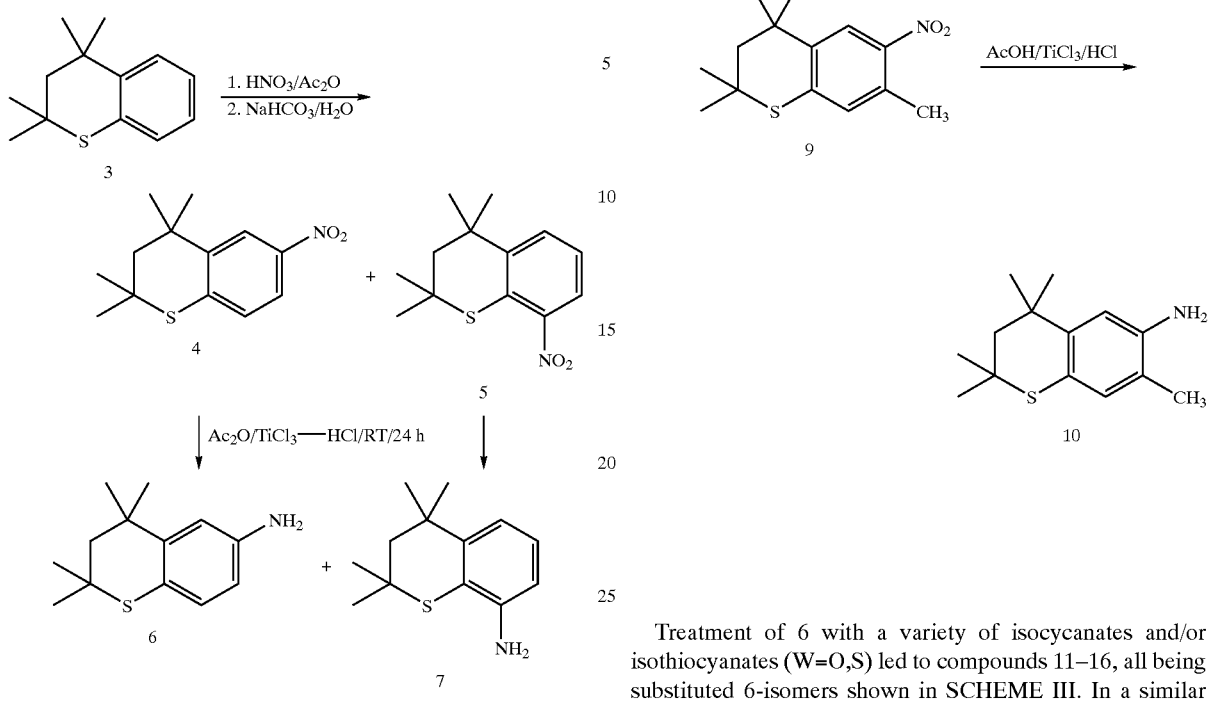

Treatment of 6 with a variety of isocycanates and/or isothiocyanates (W=O,S) led to compounds 11–16, all being substituted 6-isomers shown in SCHEME III. In a similar manner, treatment of 10 with isocyanates or isothiocyanates gave compounds 17–21. All members of 11–21 were purified and identified by spectroscopic techniques. Members of the 8-isomer family were prepared from 7 and gave 22–24 which were purified and identified by spectroscopy and described in SCHEME IV. In addition, all products 11–24 gave satisfactory elemental analyses, confirming the structures.

SCHEME III

| G | R | W | Z | Number |
|---|---|---|---|--------|
| H | H | S | $NO_2$ | 11 |
| H | H | S | $CO_2Et$ | 12 |
| H | H | O | $CO_2Et$ | 13 |
| H | H | O | $CO_2H$ | 14 |
| H | H | S | $SO_2NH_2$ | 15 |
| $H_3C$ | H | S | $NO_2$ | 16 |
| H | $H_3C$ | S | $NO_2$ | 17 |
| H | $H_3C$ | S | $CO_2H$ | 18 |
| $H_3C$ | $H_3C$ | S | $NO_2$ | 19 |
| H | $H_3C$ | S | $SO_2NH_2$ | 20 |
| H | $H_3C$ | O | $CO_2Et$ | 21 |

SCHEME IV

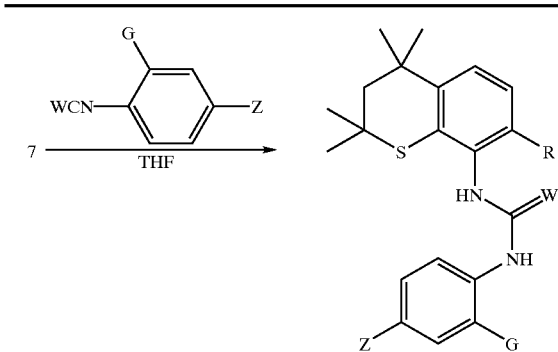

| G | R | W | Z | Number |
|---|---|---|---|--------|
| H | H | S | NO$_2$ | 22 |
| H | H | S | CO$_2$Et | 23 |
| H | H | O | CO$_2$Et | 24 |

As representative members of 1 and 2, the syntheses of a few examples, but not limited to those shown, of the oxygen-containing, isobenzopyran derivatives are delineated in SCHEMES V and VI. Starting with known structure 25, conversions to 25→26→27→28 (and 30 formed in same reaction)→29 gave the target compounds 31–36 (SCHEME V). Likewise, the 5-isomer 30 led to 37 which was converted to the final compounds 38–41 as shown in SCHEME VI.

SCHEME V

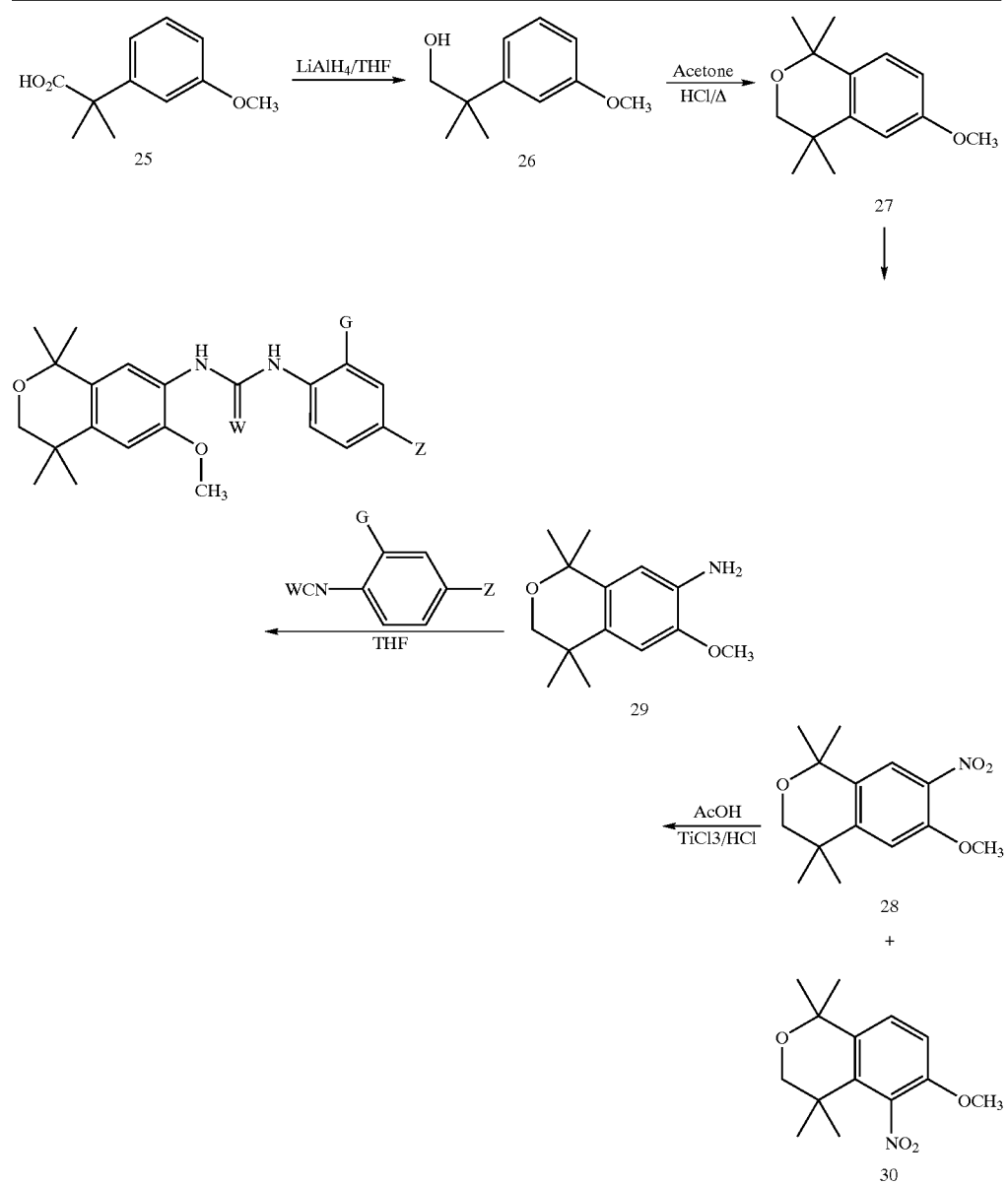

SCHEME V-continued

| G | W | Z | Number |
|---|---|---|--------|
| H | S | $NO_2$ | 31 |
| H | S | $CO_2Et$ | 32 |
| H | O | $CO_2Et$ | 33 |
| H | O | $CO_2$-n-Bu | 34 |
| $H_3C$ | S | $NO_2$ | 35 |
| $H_3C$ | S | $SO_2NH_2$ | 36 |

SCHEME VI

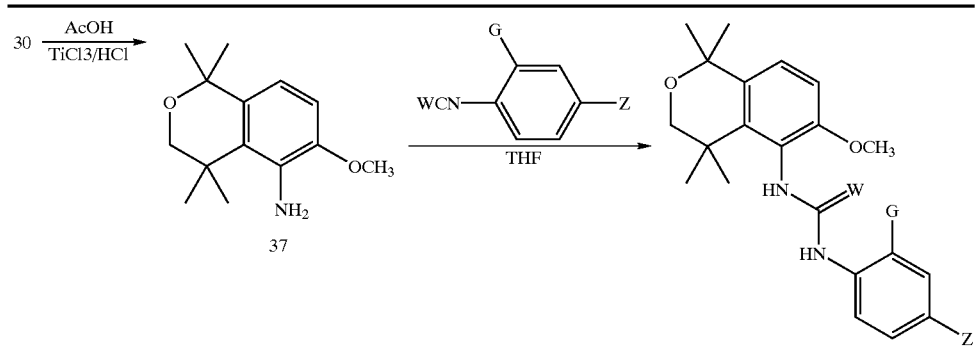

| G | W | Z | Number |
|---|---|---|--------|
| H | O | $CO_2Et$ | 38 |
| H | S | $CO_2Et$ | 39 |
| H | O | $CO_2$-n-Bu | 40 |
| H | S | $NO_2$ | 41 |

Starting from 42→43, the conversion to 43→44 followed already described procedures. Heteroarotinoids 45 and 46 were obtained from 44 via the addition to the latter of the isocyanate or isothiocyanate as illustrated in SCHEME VII. Elemental and spectral analyses confirmed the structures of 45 and 46.

SCHEME VII

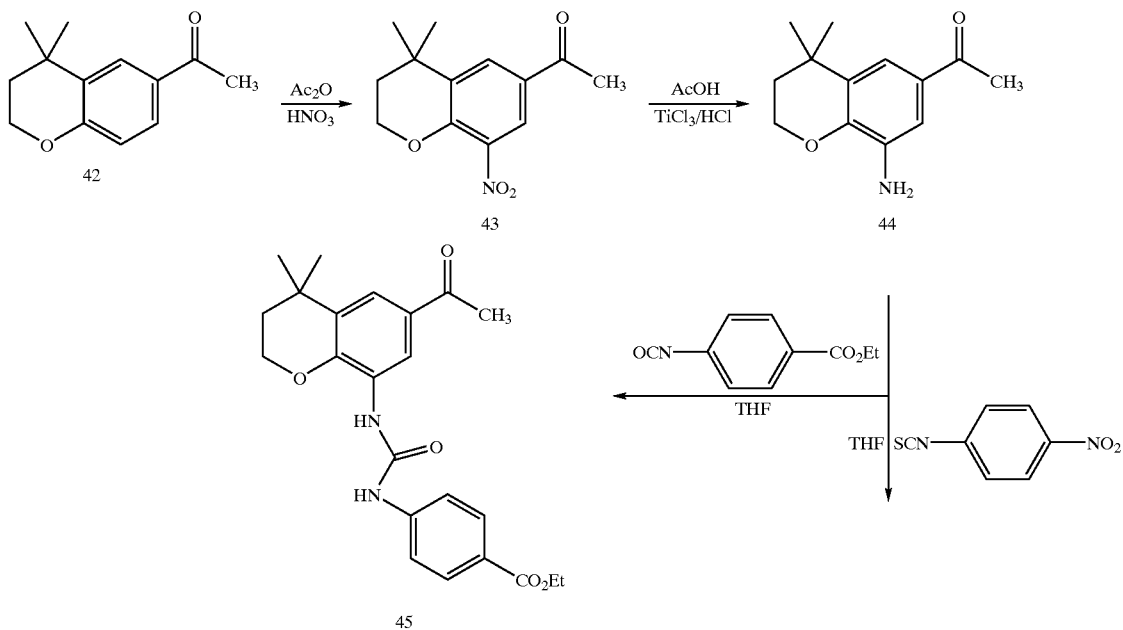

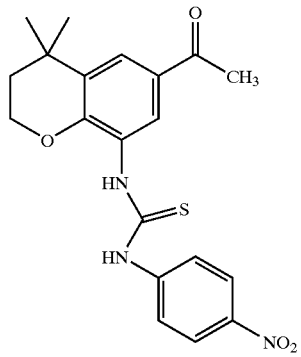

46

As an additional test of the affect of an alkyl group on one of the nitrogen atoms, 6 was converted to the key intermediate 47 which in turn was utilized to generate 48 and 49 as illustrated in Scheme VIII. In a similar manner and as a representative example for the oxygen-containing systems, 29 was converted to 50 and these to the target compound 51 as is also shown in Scheme VII. Structures 48, 49, and 51 were confirmed by both elemental and spectral analyses.

HNO$_3$ (3.54 mL) and Ac$_2$O (9 mL) dropwise, and then the mixture was stirred (2 h). The new mixture was poured into a solution of saturated aqueous NaHCO$_3$, and the resulting mixture was extracted (H$_2$CCl$_2$, 3×40 mL). After the organic solution was washed with water and brine, and, after drying (Na$_2$SO$_4$), the solvent was evaporated to a solid which was recrystallized (hexane) to give 4 (1.6 g, 27%) as a white solid, mp 103–107° C. $^1$H NMR (DCCl$_3$) δ 1.10 [s, 3 H,

SCHEME VIII

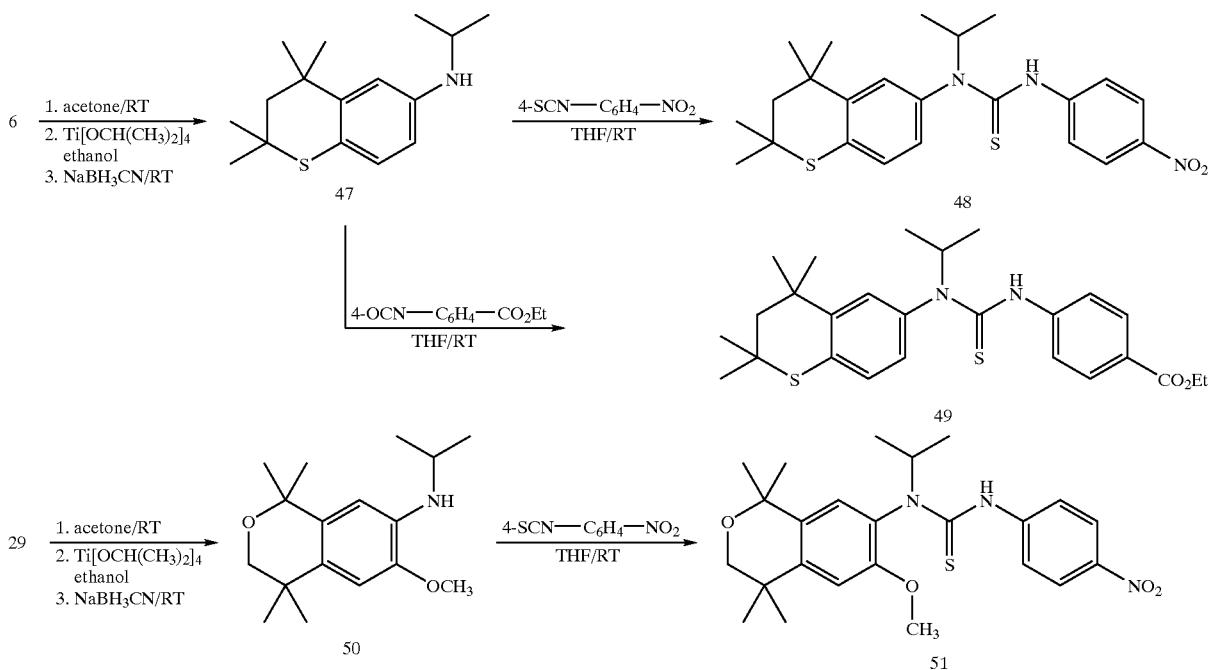

The present invention will be further understood with reference to the following non-limiting experimental examples.

EXAMPLE I 2,2,4,4-Tetramethyl-6-nitrothiochroman (4) and 2,2,3,4-Tetramethyl-8-nitrothiochroman (5)

To known thioether 3 (5.13 g, 24.86 mmol) in freshly distilled Ac$_2$O (5 mL) at 0° C. was added a cold mixture of C(CH$_3$)$_2$], 1.37 [s, 3 H, C(CH$_3$)$_2$]. 1.52 [ps, 3 H, SC(CH$_3$)$_2$], 1.56 [s, 3 H, SC(CH$_3$)$_2$], 2.03 [m, 3 H, CH$_2$], 8.01 [d, 1 H, Ar—H], 8.24 [d, 2 H, Ar—H]; 13C NMR (DCCl$_3$) ppm 18.5 [C(CH$_3$)$_2$], 26.1 [C(CH$_3$)$_2$], 32.0 [SC(CH$_3$)$_2$], 34.5 [SC(CH$_3$)$_2$], 34.75 [C(CH$_3$)$_2$, 46.3 [CH$_2$], 54.4 [SC(CH$_3$)], and Ar—C [121.6, 121.8, 127.9, 128.3, 146.0, 146.5].

The filtrate from the recrystallization solvent (hexane) was concentrated and yielded 5 as a white solid, mp 65–67° C. $^1$H NMR (DCCl$_3$) δ 1.17 [s, 3 H, C(CH$_3$)$_2$], 1.33 [s, 3 H, C(CH$_3$)$_2$], 1.40 [s, 3 H, SC(CH$_3$)$_2$], 1.46 [s, 3 H, SC(CH$_3$)$_2$], 2.16 [d, 2 H, CH$_2$], 7.40 [m, 2 H, Ar—H], 7.79 [d, 1 H, Ar—H]; $^{13}$C NMR (DCCl$_3$) ppm 19.6 [C(CH$_3$)$_2$], 25.1 [C(CH$_3$)$_2$], 32.6 [SC(CH$_3$)$_2$], 34.4 [SC(CH$_3$)$_2$], 34.6 [C(CH$_3$)$_2$], 45.2 [CH$_2$], 52.4 [SC(CH$_3$)$_2$], and Ar—C [127.0, 128.4, 130.8, 138.1, and 143.6].

Both 4 and 5 were used in the conversions to 6 and 7 without further purification.

EXAMPLE II 2,2,4,4-Tetramethyl-6-aminothiochroman (6) and 2,2,4,4-Tetramethyl-8-aminothiochroman (7)

It was found to be more efficient if the above mixture of 4 and 5 was reduced together to 6 and 7, which could be separated on silica gel. A mixture of 4 and 5 (3:2, 0.800 g, 3.18 mmol) in acetic acid (29 mL) and water was stirred vigorously for a few moments. Then a solution of TiCl$_3$/HCl (33.00 g, 21.39 mmol) was added dropwise, and the resulting mixture was stirred at room temperature for 2 h. The resulting reaction mixture was cooled (0° C.), and 30% aqueous NaOH (~130 mL) was added slowly. Extracts EtOAc (4×35 mL) and H$_2$CCl$_2$ (2×40 mL) of the aqueous layer were combined, washed with water and saturated NaHCO$_3$ and then dried (Na$_2$SO$_4$). Evaporation of the solvent and chromatography of the residual oil on silica gel (hexane:H$_2$CCl$_2$, 1:1) gave 6 (0.211 g, 30%) as a white solid (mp 45–50° C.) and 7 (0.140 g, 20%) as a solid (mp 61–63° C.). A second pass of the crude 6 through a fresh column gave a pure 6, mp of 57–59° C.

Spectral data for 6: IR (KBr) 3450–3360 (N—H) cm$^{-1}$; $^1$H NMR (DCCl$_3$) δ 1.36 [s, 6 H, C(CH$_3$)$_2$], 1.39 [s, 6 H, SC(CH$_3$)$_2$], 1.90 [s, 2 H, CH$_2$], 3.50 [bs, 2 H, NH$_2$], 6.44 [d, 1 H, Ar—H], 6.75 [s, 1 H, Ar—H], 9.92 [d, 1 H, Ar—H]; $^{13}$C NMR (DCCl$_3$) ppm 31.6 [C(CH$_3$)$_2$], 32.0 [SC(CH$_3$)$_2$], 35.7 [C(CH$_3$)$_2$], 41.8 [SC(CH$_3$)$_2$], 54.7 [CH$_2$], and Ar—C [113.7, 113.8, 121.2, 129.1, 143.9, and 144.1].

Spectral data for 7: IR (KBr) 3460–3372 (N—H) cm$^{-1}$; $^1$H NMR (DCCl$_3$) δ 1.39 [s, 6 H, C(CH$_3$)$_2$], 1.42 [s, 6 H, SC(CH$_3$)$_2$], 1.91 [s, 2 H, CH$_2$], 3.89 [bs, 2 H, NH$_2$]. 6/.56 [d, 1 H, Ar—H], 6.91 [m, 2 H, Ar—H]; $^{13}$C NMR (DCCl$_3$) ppm 31.8 [C(CH$_3$)$_2$], 31.9 [SC(CH$_3$)$_2$], 36.0 [C(CH$_3$)$_2$], 42.2 [SC(CH$_3$)$_2$], 54.4 [CH$_2$], and Ar—C [112.3, 116.6, 117.7, 125.0, 143.5, and 144.4].

EXAMPLE III

6-Nitro-2,2,4,4,7-pentamethylthiochroman (9) and 6-Amino-2,2,4,4,7-pentamethylthiochroman (10)

Thio ether 8 (22.00 g, 99.83 mmol) in Ac$_2$O (23 mL) was treated dropwise with cold, concentrated HNO$_3$ (23 mL) at -5° C., and then the mixture was stirred (1 h). The resulting mixture was poured into a solution of saturated NaHCO$_3$, and the newly formed mixture was extracted (H$_2$CCl$_2$, 3×200 mL). After the extracts were washed with water and brine, the organic layer was dried (Na$_2$SO$_4$) and then evaporated to an oil which was distilled (bp 160–162° C.) to a thick oil (7 g, 26%). The oil 9 was used immediately to prepare 10 without further purification.

Spectral data for 9: $^1$H NMR (DCCl$_3$) δ 1.11 [s, 3 H, CH$_3$], 1.33 [s, 3 H, CH$_3$], 1.50 [s, 3 H, OCCH$_3$], 1.51 [s, 3 H, CH$_3$], 2.03 [s, 2 H, CH$_2$], 2.64 [s. 3 H, OCH$_3$], 2.64 [s, 3 H, OCH$_3$], 7.78 [s, 1 H, Ar—H], 7.97 [s, 1 H, Ar—H].

Ether 9 (1.0 g, 3.77 mmol) in AcOH ((36 mL) and water (7 mL) was stirred vigorously, and then TiCl$_3$/HCl (40.07 g, 26.38 mmol) was added dropwise. The resulting mixture was stirred at room temperature for 7 h. The new mixture was cooled (0° C.), and a 30% aqueous solution of NaOH was added slowly. The aqueous layer was extracted (EtOAc, 4×60 mL), and the combined organic extracts were washed with water and saturated NaHCO$_3$. After the organic phase was dried (Na$_2$SO$_4$), the solvent was evaporated to an oil which was subjected to flash chromatography over silica gel (hexanes:EtOAc, 10:1). Fractions were collected which contained 0.400 g (45%) of 10 as a dark yellow oil. The oil was used without further purification.

Spectral data for 10: IR (neat) 3459 (N—H) cm$^{-1}$; $^1$H NMR (DCCl$_3$) δ 1.35 [s, 6 H, C(CH$_3$)$_2$], 1.37 [s, 6 H, OC(CH$_3$)$_2$], 1.89 [s, 2 H, CH$_2$], 2.09 [s, 3 H, OCH$_3$], 3.23 [s, 2 H, NH$_2$], 6.74 [s, 1 H, Ar—H], 7.83 [s, 1 H, Ar—H].

EXAMPLE IV

[N-(4-Nitrophenyl)amino][2,2,4,4-tetramethyl{3H-benzo[3,4-e]thiany-6-yl})amino]methane-1-thione (11) and Analogs Thereof (12–21)

To a solution of 6 (0.200 g, 0.9 mmol) in THF (4 mL) at 0° C. was added dropwise 4-nitrophenylisocyanate (170 mg, 0.9 mmol) in THF (5 mL) under N$_2$. When the addition was complete, the mixture was stirred overnight. Evaporation of the solvent gave a solid which was recrystallized (pentane: HCCl3; 1:1) to yield a very light yellow solid 11, mp 153–155° C. $^1$H NMR (DCCl$_3$) δ 1.39 [s, 6 H, C(CH$_3$)$_2$], 1.44 [s, 6 H, SC(CH$_3$)$_2$], 1.97 [s, 2H, CH$_2$], 7.18 [d, 2 H, Ar—H], 7.23 [d, 1 H, Ar—H], 7.34 [d, 1 H, Ar—H], 7.24 [d, 2 H, Ar—H]], 7.96 [bs, 1 H]], 8.20 [d, 2 H, Ar—H], 8.44 [bs, 1 H]; $^{13}$C NMR (DCCl$_3$) ppm 31.4, 32.3, 35.7, 42.3, 53.5, and Ar—C [122.9, 123.0, 124.1, 124.6, 129.5, 132.2, 133.9, 143.9, 144.5, and 145.1], and 179.0 (C═O). Anal. Calcd for C$_{20}$H$_{23}$N$_3$O$_2$S$_2$: C, 59.82; H, 5.77; 10.46; S, 15.97. Found: C, 59.79; H, 5.79; N, 10.54; S, 15.87.

Other examples including members of 12–16 were prepared in an identical fashion from 6 while 17–21 were obtained from 10 in a like manner. The products 12–21 gave the following physical data.

12: mp 134–135° C.; $^1$H NMR (DCCl$_3$) δ 1.38 [s, 6 H], 1.40 [t, 2 H], 1.43 [s, 6 H], 1.95 [s, 2 H], 4.35[q, 2 H], 7.04 [dd, 1 H], 7.16 [d, 1 H, Ar—H], 7.36 [d, 1 H, A r—H], 7.55 [d, 2 H, Ar—H], 8.00 [s, 1 H, NH], 8.02 [d, 2 H, Ar—H], 8.35 [s, 1 H, NH]; $^{13}$C NMR (DCCl$_3$) ppm 31.4, 32.2, 35.6, 42.0, 54.1, 60.9, and Ar—C [118.4, 120.0, 120.6, 124.8, 130.9, 134.4, 142.9, and 144.2], and 153.3 (C═O) and 166.7 (C═O). Calcd for C$_{23}$H$_{28}$N$_2$O$_2$S$_2$: C, 64.45; H, 6.58; N, 6.53; S, 14.96. Found: C, 64.57; H, 6.66; N, 6.57; S, 14.86.

13: mp 200–201° C.; $^1$H NMR (DCCl$_3$) δ 1.32, 1.35, 1.37, 1.40, 1.89, 4.35, 6.9–7.56 (m), 7.91. Calcd for C$_{23}$H$_{28}$N$_2$O$_3$S: C, 66.96; H, 6.84; N, 6.79; S, 7.77. Found: C, 67.04; H, 6.86; N, 6.83; S, 7.83.

14: mp 293° C. (dec); IR (KBr) 3359 (O—H), 1696 (C═O) cm$^{-1}$; $^1$H NMR DMSO-d$_6$) δ 1.89, 3.34, 6.96 [d], 7.17 [dd], 7.56 [m], 7.85 [d], 8.70 [s], and 8.99 [s]; $^{13}$C NMR (DMSO-d$_6$) ppm 31.2, 32.2, 35.3, 53.7, and Ar—C [117.2, 117.33, 117.38, 123.6, 125.0, 128.0, 130.7, 136.9, 143.1, 144.2], and 152.4 [C═O], and 167.2 [C═O]. Calcd for C$_{21}$H$_{24}$N$_2$O$_3$S: C, 65.60; H, 6.29; N, 7.29; S, 8.34. Found: C, 65.60; H, 6.28; n, 7.25; S, 8.34.

15: mp 191–193° C.; IR (KBr) 3358, 3272 (N—H) cm$^{-1}$; $^1$H NMR (DMSO-d$_6$) δ 1.32, 1.37, 1.91, 7.01, 7.24, 7.60, 9.98; $^{13}$C NMR (DMSO-d$_6$) ppm 31.2, 32.2, 35.2, 42.0, 53.4, and Ar—C [122.0, 126.3, 127.4, 128.1, 136.4, 139.1, 142.6] and 179.4 (C═O). Calcd for C$_{20}$H$_{25}$N$_3$O$_2$S$_3$; C, 55.14,; H, 5.79; N, 9.65; S, 22.08. Found: C, 55.15; H, 5.82; N, 9.62; S, 22.12.

16: mp 155–156° C.; IR (KBr) 3344, 3120 (N—H) cm$^{-1}$; $^1$H NMR (DCCl$_3$) δ 1.40, 1.43, 1.97, 2.25, 7.06, 7.24, 7.37, 7.42, 8.06; $^{13}$C NMR (DCCl$_3$) ppm 17.9, 31.4, 32.3, 35.7, 42.4, 53.6, and Ar—C [122.1, 123.7, 124.8, 125.8, 126.4, 129.6, 132.3, 133.5, 134.4, 142.4, 145.3, 145.4], and 179.9 (C=O). Calcd for C$_{21}$H$_{25}$N$_3$O$_2$S$_2$: C, 60.60; H, 6.06; N, 10.11; S, 15.43. Found: C, 60.41; H, 6.01; N, 9.93; S, 15.51.

17: mp 172–173° C.; IR (KBr) 3345, 3160 (N—H) cm$^{-1}$; $^1$H NMR (DCCl$_3$) δ 1.38, 1.44, 1.96, 2.52, 7.10, 7.30, 7.60, 7.75, 8.00; $^{13}$C NMR (DCCl$_3$) ppm 17.1, 31.5, 32.7, 35.4, 42.4, 53.6, and Ar—C [123.0, 12.4, 125.9, 130.5, 136.6, 133.2, 134.9, 142.5, 143.9, 144.5] and 179.5. Calcd for C$_{21}$H$_{25}$N$_3$O$_2$S$_2$: C, 60.69; H, 6.06; N, 10.11; S, 15.43. Found: C, 60.77; H, 6.09; N, 10.02; S, 15.53.

18: mp 266° C. (dec); IR (KBr) 3366, 3167 (N—H) cm$^{-1}$; $^1$H NMR (DMSO-d$_6$) δ 1.31, 1.37, 1.90, 2.16, 6.93, 7.34, 7.30, 7.65, 7.66, 7.87, 9.52, 9.97. $^{13}$C NMR (DMSO-d$_6$) ppm 17.1, 31.2, 32.4, 34.8, 38.6, 41.9, 534, and Ar—C [121.8, 121.9, 125.6, 126.3, 128.6, 129.7, 132.5, 134.6, 139.9, 143.8], and 166.9, 180.0 (C=O). C$_{22}$H$_{26}$N$_2$O$_2$S$_2$: C, 63.73; H, 6.32; N, 6.76; S, 15.47. Found: C, 63.77; H, 6.21; N, 6.76; S, 15.60.

19: mp 174–175° C.; IR (KBr) 3302, 3174 (N—H) cm$^{-1}$; $^1$H NMR (DCCl$_3$) δ 1.38, 1.43, 1.96, 2.16, 2.82, 7.11, 7.35, 8.06, 8.10, 8.25; $^{13}$C NMR (DCCl$_3$) ppm 17.1, 17.8, 31.5, 32.6, 35.4, 42.4, 53.7, and Ar—C [121.9, 125.7, 126.3, 126.4, 130.6, 133.3, 133.7, 135.2, 142.3, 142.5, 145.3] and 179.8. Calcd for C$_{22}$H$_{27}$N$_3$O$_2$S$_2$: C, 61.51; H, 6.33; N, 9.78; S, 14.93. Found C, 61.49; H, 6.26; N, 9.63; S, 14.95.

20: mp 190–192° C.; IR (KBr) 3366, 3267 (N—H) cm$^{-1}$; $^1$H NMR (DCCl$_3$) δ 1.31, 1.37, 1.91, 2.16, 6.94, 7.30, 7.35, 7.36, 7.76, 9.53, 9.92; $^{13}$C NMR (DCCl$_3$) ppm 17.1, 31.2, 32.4, 34.8, 41.9, 53.4, and Ar—C [122.6, 122.7, 126.0, 126.3, 128.6, 129.8, 132.5, 134.5, 139.9, 142.7] and 180.2. Calcd for C$_{21}$H$_{27}$N$_3$O$_2$S$_3$: C, 56.09; H, 6.05; N, 9.34; S, 21.39. Found: C, 56.14; H, 6.06; N, 9.28; S, 21.45.

21: mp 128–129° C.; IR (KBr) 3310, 3203 (N—H), 1716 (C=O) cm$^{-1}$; δ$^1$H NMR (DCCl$_3$) δ 1.34, 1.38, 1.89, 2.12, 4.33, 6.86, 6.95, 7.32, 7.49, 7.53, 7.89. $^{13}$C NMR (DDCl$_3$) ppm 14.3, 17.1, 31.5, 32.5, 35.3, 42.1, 54.0, 60.8, and Ar—C [118.2, 124.0, 124.6, 129.9, 130.4, 130.7, 132.0, 141.6, 142.8, 154.8], and 166.4, 179.6. Calcd for C$_{24}$H$_{30}$N$_2$O$_2$S: C, 67.58; H, 7.09; N, 6.57; S, 7.52. Found: C, 67.66; H, 7.21; N, 6.54; S, 7.44.

EXAMPLE V

[(4-Nitrophenyl)amino][(2,2,4,4-tetramethyl{3H-benzo[3,4-e]thiany-8-yl})amino]methane-1-thione (22) and Analogs Thereof (23 and 24)

Treatment of slightly crude amine 7 (0.200 g, 0.90 mmol) in THF (5 mL) was treated dropwise with 4-nitrophenylisothiocyanate (0.63 g, 0.90 mmol) in THF at 0–5° C. under N$_2$. The mixture was allowed to warm to room temperature and then was stirred overnight. Removal of the solvent gave a solid which was recrystallized (ether) and gave pure 22 (0.110 g, 30%), mp 137° C. (dec); IR (KBr) 3100 (N—H) cm$^{-1}$; $^1$H NMR (DCCl$_3$) δ 1.39, 1.40, 1.96, 7.18, 7.43, 7.71, 7.96, 8.17; $^{13}$C NMR (DCCl$_3$) ppm 31.4, 32.7, 35.8, 42.5, 53.6, and Ar—C [120.4, 123.3, 124.6, 125.1, 125.2, 127.2, 132.1, 143.9, 144.7, 145.7] and 178.9. Calcd for C$_{20}$H$_{23}$N$_3$O$_2$S$_2$: C, 59.82; H, 5.77; N, 10.47; S, 15.97. Calcd for C$_{20}$H$_{23}$N$_3$O$_2$S$_2$ 0.25 H$_2$O : C, 59.16; H, 5.71; N, 10.35; S, 15.79. Found: C, 59.17; H, 5.76; N, 10.31; S, 15.82.

In a similar manner, 23 and 24 were prepared from 7 and ethyl 4-isocyanantobenzoate and ethyl 4-iosthiocyanatobenzoate, respectively. Esters 23 and 24 gave the following physical data.

23: mp 143–144° C.; IR (KBr) 1712 cm$^{-1}$; $^1$H NMR (DCCl$_3$) δ 1.38, 1.40, 1.41, 1.96, 4.36 7.16, 7.36, 7.56, 7.79, 7.88, 8.02; $^{13}$C NMR (DCCl$_3$) ppm 31.4, 32.5, 35.8, 42.3, 53.7, 60.9, and Ar—C [123.4, 124.5, 124.9, 126.4, 127.6, 1'30.6, 131.3, 133.0, 141.9, 145.2] and 166.0, 179.6. Calcd for C$_{23}$H$_{28}$N$_2$O$_2$S$_2$: C, 64.45; H, 6.58; N, 6.54; S, 14.96. Found: C, 64.41; H, 6.57; N, 6.54; S, 14.98.

24: mp 155–156° C.; IR (KBr) 3387, 3258, (N—H), 1715 (C=O), 1672 (C=O) cm$^{-1}$; $^1$H NMR (DCCl$_3$) δ 1.26, 1.34, 1.36, 1.85, 4.34, 7.05, 7.19, 7.24, 7.47, 7.89, 8.03; $^{13}$C NMR (DCCl$_3$) ppm 14.1, 31.5, 32.2, 35.9, 42.4, 53.8, 60.7, and Ar—C[118.3, 121.8, 123.4, 124.2, 124.9, 126.9, 130.8, 134.0, 144.4] and 153.5, 166.8. Calcd for C$_{23}$H$_{28}$N$_2$O$_3$S: C, 66.96; H, 6./84; N, 6.79; S, 7.77. Found: C, 67.01; H, 6.83; N, 6.79; S, 7.77. Base (NaOH/95% ethanol) catalyzed hydrolysis of 24 by standard conditions gave the corresponding acid derivative which was analyzed, mp 308° C. (dec); IR (KBr) 3310–2600 [C(O)—O—H], 1692 (C=O) cm$^{-1}$; $^1$H NMR (DMSO-d$_6$) δ 1.35, 1.38, 1.91, 7.07, 7.24, 7.55, 7.86, 9.60; $^{13}$C NMR (DMSO-d$_6$) ppm 31.3, 32.2, 35.6, 42.2, 53.4, and Ar—C [117.1, 120.5, 122.2, 123.6, 124.2, 124.6, 130.7, 134.9, 143.6, 144.3], and 152.5, 167.2. Calcd for C$_{21}$H$_{24}$N$_2$O$_3$S: C, 65.60; H, 6.29; N, 7.29; S, 8.34. Found: C, 65.50; H, 6.28; N, 7.25; S, 8.34.

EXAMPLE VI 1,1,4,4-Tetramethyl-6-methoxy-7-nitro-3,4-dihydro-1H-2-benzopyran (28), 1,1,4,4-Tetramethyl-6-methoxy-5-nitro-3,4-dihydro-1H-2-benzopyran (30), 1,1,4,4-Tetramethyl-6-methoxy-7-amino-3,4-dihydro-1H-2-benzopyran (29), and 1,1,4,4-Tetramethyl-6-methoxy-5-amino-3,4-dihydro-1H-2-benzopyran (37)

Treatment of 27 (18.0 g, 81.7 mmol), prepared from the reaction sequence 25→26 as found in the recent literature [*Journal of Medicinal Chemistry,* 1999, Vol. 42, pages 4434–4445, and the article is entitled "Heteroarotinoids Inhibit Head and Neck Cancer Cell Lines in vitro and in vivo Through Both RAR and RXR Retinoic Acid Receptors" by D. Zacheis, A. Dhar, S. Lu, M. M. Madler, J. Klucik, C. W. Brown, S. Liu, F. Clement, S. Subramanian, G. M. Weerasekare, K. D. Berlin, M. A. Gold, J. R. Houch, Jr., K. R. Fountain, and D. M. Benbrook.], dropwise with a mixture of cold, concentrated HNO$_3$ (18 mL and Ac$_2$O (36 ml) at −5 to −8° C. gave a solution which was stirred for 1 h. The mixture was poured into a saturated aqueous solution of aqueous NaHCO$_3$ (300 mL), and the resulting mixture was extracted (H$_2$CCl$_2$). After separation, the aqueous layer was washed with water and brine and then dried (Na$_2$SO$_4$). Evaporation of the solvent gave an oil which was triturated with pentane to yield a solid that was recrystallized (95% ethanol) to give 28 (13.49 g, 63%), mp 124–125° C. $^1$H NMR (DCCl$_3$) δ 1.28, 1.51, 3.58, 3.94, 6.94, 7.59; $^{13}$C NMR (DCCl$_3$) ppm 26.6, 29.5, 34.5, 56.4, 70.1, 74.6, and Ar—C [110.2, 122.1, 134.5, 137.7, 150.2, 151.5]. MS (EI) calcd for C$_{14}$H$_{19}$NO$_4$ (M$^+$): 265. Found: 265.

Additional chromatography on silica gel (hexane:ether, 9:1) of the filtrate gave a solid which was recrystallized (95% ethanol) to yield 30 (6.91 g, 32%), mp 82–83° C. $^1$H NMR (DCCl$_3$) δ 1.28, 1.51, 3.48, 3.83, 6.88, 7.12; $^{13}$C NMR (DCCl$_3$) ppm 24.0, 30.0, 34.1, 56.3, 71.6, 74.1, and Ar—C [110.6, 128.1, 134.5, 135.5, 140.8, 159.3; MS (EI) calcd for C$_{14}$H$_{19}$NO$_4$ (M$^+$): 265. Found: 265. Compounds 28 and 30 were used immediately without further purification to prepare 29 and 37, respectively.

To 28 (7.0 g, 26.38 mmol) in AcOH (250 mL) and water (5 mL) vigorously stirred was added dropwise $TiCl_3/HCl$ (400.g, 259.3 mmol) which was followed by stirring for 7 h at room temperature. The resulting mixture was cooled (0° C.), and 30% aqueous NaOH was added (1 L). Separation and extraction (EeOAc, 8×200 mL) gave an organic layer which was washed with water and saturated aqueous $NaHCO_3$ and then was dried ($Na_2SO_4$). Evaporation of the solvent gave a solid which was recrystallized (95% ethanol) to give 29 (5.05 g, 81%), mp 126–127° C.; IR (Kbr) 3449, 3188 (N—H); $^1H$ NMR ($DCCl_3$) δ 1.24, 1.48, 3.56, 3.64, 3.85, 6.41, 7.67; $^{13}C$ NMR ($DCCl_3$) ppm 27.0, 29.7, 33.4, 55.4, 71.1, 74.8, and Ar—C [106.7, 111.7, 132.7, 134.0, 146.2]. MS (EI) calcd for $C_{14}H_{19}NO_4$ ($M^+$): 235. Found: 235.

To 30 (5.7 g, 17.7 mmol) in AcOH (206 mL) and water (42 mL) with vigorous stirring was added dropwise $TiCl_3/HCl$ (30%, 120 g, 177.1 mmol). After stiring at room temperature for 13 h, the mixture was cooled (0° C.), and 30% aqueous NaOH (500 mL) was added cautiously. The combined extracts (EtOAc, 8×100 mL) of the aqueous layer were washed with water and a saturated aqueous solution of $NaHCO_3$ and then was dried ($Na_2SO_4$). Evaporation of the solvent gave a solid which was recrystallized (95% ethanol) to give pure 37 (3.0 g, 58%), mp 110–112° C.; IR (KBr) 3449, 3338 (N—H); $^1H$ NMR ($DCCl_3$) δ 1.37, 1.49, 3.53, 3.83, 3.98, 6.50, 7.69; $^{13}C$ NMR ($DCCl_3$) ppm 27.0, 29.7, 33.4, 55.4, 71.7, 74.8, and Ar—C [106.7, 111.7, 132.7, 134.0, 146.2]. MS (EI) calcd for $C_{14}H_{19}NO_4$ ($M^+$): 235. Found: 235.

EXAMPLE VII

[(6-Methoxy-1,1,4,4-tetramethylisochroman-7-yl)amino][(4-nitrophenyl)amino]methane 1-Thione (31) and Analogs Thereof (32–36)

A solution of 29 (0.200 g, 0.85 mmol) in THF (4 mL) was treated dropwise with a solution of 4-nitrophenylisothiocyanate (0.169 g, 0.94 mmol) in THF (5 mL) at 0° C. under $N_2$. After the mixture had warmed to room temperature, it was stirred overnight. Evaporation of the solvent gave an oil which crystallized and then was recrystallized (pentane:$H_2CCl_2$, 3:1) to yield 31 as a light yellow solid (0.300 g, 83%), mp 178–179° C. IR 3373, 3300 (N—H); $^1H$ NMR ($DCCl_3$) δ 1.29, 1.51, 3.60, 3.89, 6.88, 7.27, 7.44, 7.68, 8.02, 8.24; $^{13}C$ NMR ($DCCl_3$) ppm 26.8, 29.7,34.1, 55.9, 70.5, 74.8, and Ar—C [108.4, 122.0, 122.4, 123.2, 124.9, 135.0, 143.1, 143.8, 144.5, 150.4], and 178.7 (C=S). Calcd for $C_{21}H_{25}N_3O_4S$: C, 60.70; H, 6.07; N, 10.11; S, 7.72. Found: C, 60.42; H, 5.98; N, 10.10; S, 7.65.

In a similar manner, 32–36 were prepared from 29 and the required substituted isothio- or isocycanate. Compounds 32–36 gave the following physical data.

32: mp 166–168° C. IR (KBr) 3351, 3171 (N—H), 1715 (C=O) cm$^{-1}$; $^1H$ NMR ($DCCl_3$) δ 1.27, 1.39, 1.52, 3.59, 3.83, 4.38, 6.81, 7.49, 7.78, 8.06, 8.25; $^{13}C$ NMR ($DCCl_3$) ppm 14.1, 26.7, 29.6, 33.9, 55.8, 61.0, 70.6, 74.9, and Ar—C [107.6, 121.5, 122.7, 124.12, 127.73, 131.03, 134.33, 141.50, 141.71, 149.80], 165.91 (C=O), and 178.42 (C=S). Calcd for $C_{21}H_{25}N_3O_4S$: C, 65.13; H, 6.83; N, 6.33; S, 7.25. Found: C, 64.93; H, 6.82; N, 6.29; S,7.20.

33: mp 142–144° C. IR (KBr) 3351, 3171(N—H), 1715 (C=O) cm$^{-1}$; $^1H$ NMR ($DCCl_3$) δ 1.25 [s, 6 H, $CC(CH_3)_2$], 1.38 [t, 3 H, J=7.1 Hz, $CH_3$], 1.53 [s, 6 H, $OC(CH_3)_2$], 3.58 [s, 2 H, $CH_2$], 3.80 [s, 3 H, $OCH_3$], 4.36 [q, 2 H, J=7.0 Hz, $CH_2$], 6.74 [s, 1 H, Ar—H(5)], 7.36 [s, 1 H, N(9)H], 7.48 [d, 2 H, J=9.1, Ar—H(13), Ar—H(17)], 7.50 [s, 1 H, N(11)H], 7.83 [s, 1 H, Ar—H(8)], 7.97 [d, J=8.8 Hz, Ar—H(14), Ar—H(16)]; $^{13}C$ NMR ($DCCl_3$) ppm 14.32, [$C(CH_3)_2$], 26.98 [$OC(CH_3)_2$], 29.68 [$CH_3$], 33.82 [$C(CH_3)_2$], 55.68 [$SC(CH_3)_2$], 60.88 [$CH_2$], 70.78 [$CH_2$], 75.23 [$OCH_3$], and Ar—C [106.6, 117.0, 118.2, 124.6, 125.5, 130.8, 134.3, 137.6, 143.0, 147.0], 152.31 [NHCONH], and 166.54 [C=O]. Calcd for $C_{24}H_{30}N_2O_5$: C, 67.58; H 7.09; N, 6.57. Found: C, 67.47; H, 7.16; N, 6.49.

34: mp 148–149° C. IR (KBr) 3423, 3310 (N—H), 1716 (C=O), cm$^{-1}$; $^1H$ NMR ($DCCl_3$) δ 1.01, 1.29, 1.47, 1.53, 1.75, 3.62, 3.84, 4.35, 6.78, 7.38, 7.49, 7.53, 7.87, 8.02; $^{13}C$ NMR ($DCCl_3$) ppm 13.6, 19.2, 26.9, 29.6, 29.6, 33.8, 55.6, 64.7, 70.7, 75.2, and Ar—C [106.6, 117.1, 118.3, 124.7, 125.5, 130.9, 134.4, 137.8, 143.1, 147.1], 152.3 [NHCONH], and 166.7 [C=O]. Calcd for $C_{26}H_{34}N_2O_5$: C, 68.70; H, 7.54; N, 6.16. Found: C, 68.55; H, 7.50; N, 6.10.

35: mp 176–177° C. IR (KBr) 3224, 3125 (N—H), cm$^{-1}$; $^1H$ NMR ($DCCl_3$) δ 1.31, 1.55, 2.39, 3.63, 3.89, 6.84, 7.60, 7.74, 7.87, 8.07–8.12; $^{13}C$ NMR ($DCCl_3$) ppm 18.0, 26.8, 29.7, 34.1, 55.9, 70.5, 74.8, and Ar—C [108.0, 122.1, 122.4, 123.3, 126.0, 126.1, 133.9, 134.7, 142.0, 142.9, 145.4, 150.5], and 179.3 [C=S]. Calcd for $C_{22}H_{27}N_3O_4S$: C, 61.52; H, 6.34; N, 9.78; S, 7.46. Found: C, 61.64; H, 6.34; N, 9.72; S, 7.46.

36: mp 198–199° C. IR (KBr) 3311 (broad, N—H) cm$^{-1}$; $^1H$ NMR ($DCCl_3$) δ 1.23, 1.42, 3.50, 3.84, 6.95, 7.29, 7.67, 7.77, 9.33, 10.19; $^{13}C$ NMR (DMSO-$d_6$) ppm 26.5, 29.5, 33.6, 55.7, 69.9, 74.3, and Ar—C [107.7, 122.4, 122.9, 125.1, 126.0, 132.7, 139.0, 140.0, 142.5, 150.3], and 179.17 [C=S]. Calcd for $C_{21}H_{27}N_3O_4S_2$: C, 56.10; H, 6.05; N, 9.35; S, 14.26. Found: C, 55.95; H, 6.02; N, 9.22; S, 14.21.

EXAMPLE VIII

Ethyl 4-{[N-(6-Methoxy-1,1,4,4-tetramethylisochroman-5-yl)carbamoyl]amino}benzoate (38)

Amine 37 (200 mg, 0.85 mmol) was dissolved with 5 mL of dry THF in dried equipment and was then cooled to -5° C. Ethyl 4-isocyanatobenzoate (170.6 mg, 8.92 mmol, 1.05 eq) dissolved in 5 mL of dry THF was added dropwise. After addition, the reaction mixture was allowed to warm to RT and was stirred for 24 h. Evaporation of the solvent gave a solid which was recrystallized ($H_2CCl_2$:pentane, 2:1) to afford 38 (mp 147–9° C., 265 mg, 73%) as a white solid. IR (KBr) 3442, 3432(N—H), 1732(C=O) cm$^{-1}$; $^1H$ NMR ($DCCl_3$) δ 1.23 [t, 3 H, $OCH_2CH_3$], 1.26 [s, 6 H, $C(CH_3)_2$], 1.36 [s, 6 H, $C(CH_3)_2$], 3.17 [s, 2 H, $OCH_2$], 3.85 [s, 3 H, Ar—$OCH_3$], 4.23 [q, 2 H, $^-OCH_2$], 6.90 [d, 1 H, J=7.3 Hz, Ar—H], 7.15 [d, 1 H, J=7.3 Hz, Ar—H], 7.23 [bs, 1 H, N—H], 7.58 [d, 1 H, J=7.6 Hz, Ar—H], 7.84 [d, 1 H, J=7.6 Hz, Ar—H], 9.18 [bs, 1 H, N—H]; $^{13}C$ NMR ($DCCl_3$) ppm 25.9 [$C(CH_3)_2$], 28.6 [$C(CH_3)_2$], 34.9 [$OCH_2CH_3$], 51.4 [$C(CH_3)$], 54.8 [$C(CH_3)$], 71.7 [$(CH_3)_2OCH_2$], 105.2 [Ar—$OCH_3$], 116.8–146.7 [Ar—C], 163.4 [C=O], and 166.47 [C=O]; Calcd. for $C_{25}H_{30}N_2O_5$: C, 67.58; H, 7.08; N, 6.56. Found: C, 67.50; H, 7.10; N, 6.48.

In a similar manner, 39–41 were prepared from 37 and the required substituted isothio- or isocycanate. Compounds 39–41 gave the following physical data.

39: mp 166–167° C. $^1H$ NMR($DCCl_3$) δ 1.34, 1.37, 1.39, 1.53, 1.74, 1.83, 3.52, 3.85, 4.34, 6.91, 7.17, 7.28, 7.53, 7.99; $^{13}C$ NMR ($DCCl_3$) ppm 14.1, 24.7, 29.8, 34.1, 56.0, 60.8, 72.0, 110.3, 114.0, 121.6, 123.7, 127.5, 128.0, 130.2, 136.5, 142.6, 154.2, 166.0, 180.7. Calcd for $C_{24}H_{30}N_3O_4S$: C, 65.13; H, 6.83; N, 6.33; S, 7.24. Found: C, 65.14; H, 6.88; N, 6.48; S, 7.19.

40: mp 196–198° C. $^1H$ NMR ($DCCl_3$) δ 0.95–1.38 (m), 1.41–1.55 (m), 1.66–181 (m), 3.33, 3.76, 4.22, 6.76, 6.79, 6.97, 7.00, 7.27, 7.56; $^{13}$C NMR (DCCl$_3$) ppm 13.6, 16.1, 24.9, 30.6, 33.9, 34.4, 55.8, 55.9, 64.4, 72.1, 75./0, 75.9, 109.7, 117.7, 118.0, 122.9, 123.1, 130.5, 135.5, 142.2, 143.1, 154.9, 155.5, 166.1. Calcd for C$_{26}$H$_{24}$N$_2$O$_5$: C, 68.70; H, 7.54; N, 6.15. Found: C, 68.81; H, 7.60; N, 6.07.

41: mp 181–182° C. IR (KBr) 3226, 3132 (N—H) cm$^{-1}$, $^1$H NMR (DCCl$_3$) δ 1.28, 1.48, 3.58, 3.83, 6.84, 7.25, 7.60, 7.81, 8.15, 8.18; $^{13}$C NMR (DCCl$_3$) ppm 26.8, 29.7, 55.4, 70.5, 74.8, 108.6, 122.1–150.5, 169.4. Calcd. for C$_{21}$H$_{25}$O$_4$N$_3$S: C, 60.70; H, 6.06; N, 10.11; S, 7.71. Found: C, 60.63; H, 6.01; N, 10.11; S, 7.69.

EXAMPLE IX

Ethyl 4-{[N-(6-Acetyl-4,4-dimethylchroman-8-yl) carbamoyl]amino}benzoate (45) and N-[(6-Acetyl-4,4-dimethylchroman-8-yl)](4-nitrophenyl)amino] carboxamide (46)

To 4,4-dimethylchroman-6-yl methyl ketone (42, 5.5 g, 26.93 mmol) dissolved in Ac$_2$O (12 mL) at –8° C. was added dropwise a mixture of cold, concentrated HNO$_3$ (6 mL) and Ac$_2$O (12 mL) over 10 min after which time the mixture was stirred (1 h). The resulting mixture was then poured into a solution of saturated aqueous NaHCO$_3$ (100 mL), and the resulting mixture was extracted (H$_2$CCl$_2$, 3×40 mL). The organic layer was washed with water (50 mL) and brine (50 mL) and was then dried (Na$_2$SO$_4$). The solvent was evaporated to a thick yellow oil which was triturated with pentane to give a light yellow solid (5 g, 75%). Recrystallization (CH$_2$Cl$_2$:pentane 3:1) gave pure 43 (8-nitro-4,4-dimethylchroman-6-yl)methyl ketone (4.14 g, 62%) as a light yellow solid, mp 117–119° C. IR (KBr) 1360 (NO$_2$) cm$^{-1}$; $^1$H NMR (DCCl$_3$) δ 1.41 [s, 6 H, C(CH$_3$)$_2$], 1.95 [s, 2 H, CCH$_2$], 2.59 [s, 3 H, COCH$_3$], 4.42 [t, 2 H, OCH$_2$], 8.15 [d, 1 H, Ar—H], 8.20 [d, 1 H, Ar—H]; $^{13}$C NMR (DCCl$_3$) ppm 26.1, 30.5, 31.0, 35.8, 64.6, 124.1, 128.5, 130.8, 135.2, 139.1, 151.6, 195.3. The sample of 43 was used to prepare 44 without further purification.

To the nitro compound 43 (4.22 g, 16.93 mmol) in acetic acid (150 mL) and water (31 mL) was added dropwise TiCl$_3$(10%)/HCl (216 g, 169.3 mmol), and the final solution was strirred vigorously (7 h, RT). The new mixture was cooled (0° C.), and NaOH (30%, 600 mL) was added. The aqueous layer was extracted (EtOAc, 8×150 mL), and the combined organic layers were washed with water (2×70 mL) and saturated NaHCO$_3$ (2×100 mL). The solution was then dried (Na$_2$SO$_4$). Evaporation of the solvent give 2.97 g (80%) of amine 44 [(8-amino-4,4-dimethylchroman-6-yl) methyl ketone] as a red thick oil. IR (KBr) 3449, 3338 (N—H), cm$^{-1}$; $^1$H NMR (DCCl$_3$) δ 1.37 [s, 6 H, C(CH$_3$)$_2$], 1.85 [t, 2 H, C(CH$_2$)], 2.52 [s, 3 H, COCH$_3$], 3.84 [s, 2 H, NH$_2$], 4.30 [t, 2 H, OCH$_2$], 7.15 [d, 1 H, Ar—H], 7.3[d, 1 H, Ar—H]. $^{13}$C NMR (DCCl$_3$) ppm 26.1, 30.7, 37.1, 63.4, 112.0, 117.9, 129.8, 130.9, 135.5, 145.7, 197.6. The compound 44 was used without further purification to prepare 45 and 46.

To a solution of amine 44 (0.310 g, 1.41 mmol) in THF (6 mL) was added dropwise a solution of ethyl 4-isocyanatobenzoate (0.97 g, 1.56 mmol) in THF at –5° C. under N$_2$. After the mixture had warmed to room temperature, it was stirred overnight. Evaporation of the solvent gave an oil which crystallized when treated with H$_2$CCl$_2$:pentane as a white solid 45 (0.260 g, 45%), mp 194–195° C. IR (KBr) 3409, 3295 (N—H), 1730 (C=O), 1659 (ester C=O) cm$^{-1}$; $^1$H NMR (DCCl$_3$) δ 1.28 [s, 6 H, C(CH$_3$)$_2$], 1.38 [t, 3 H, J=7.1 Hz, CH$_3$], 1.75 [t, 2 H, J=5.2 Hz, CH$_2$], 2.57 [s, 3 H, COCH$_3$], 4.12 [t, 2 H, J=5.2 Hz, OCH$_2$], 4.34 [q, 2 H, J=7.1 Hz, OCH$_2$CH$_3$], 7.50 [d, 2 H, J=8.8 Hz, Ar—H], 7.66 [d, 1 H, J=2 H, J=2.0 Hz, Ar—H], 7.80 [s, 1 H, NH], 7.94 [d, 2 H, J=2.0 Hz, Ar—H], 8.36 [s, 1 H, NH], 8.65 [s, 1 H, J=2.0 Hz, Ar—H]; $^{13}$C NMR (DCCl$_3$) ppm 14.20, 26.44, 30.49, 36.68, 60.90, 63.86, and Ar—C [118.13, 121.31, 124.38, 127.25, 129.54, 130.93, 131.36, 143.47, 146.79, 152.67], 166.89, and 198.75 [C=O]. Calcd for C$_{23}$H$_{26}$N$_2$O$_5$: C, 67.30; H, 6.38; N, 6.82. Found: C, 67.24; H, 6.49; N, 6.86.

To a solution of amine 44 (0.300 g, 1.31 mmol) in THF (6 mL) was added dropwise 4-nitrophenylisothiocyanate (0.210 g, 1.50 mmol) in THF (6 mL) at –5° C. under N$_2$. The reaction mixture was allowed to warm to room temperature and was stirred overnight. Evaporation of the solvent afforded a yellow oil. Recrystallization [95% EtOH] gave 46 (0.500 g, 91%) as a light yellow solid, mp 123° C. (dec). IR (KBr) 3383, 3110 (N—H), 1680 (C=O) cm$^{-1}$; $^1$H NMR (DCCl$_3$) δ 1.35 [s, 6 H, C(CH$_3$)$_2$], 1.90 [t, 2 H, J=5.0, CH$_2$], 2.56 [s, 3 H, C(O)CH$_3$], 3.34 [t, 2 H. J=5.3, CH$_2$], 4.62 [s, 1 H, NH], 7.83 [s, 1 H, Ar—H], 7.95 [m, 2 H, Ar—H], 8.19 [m, 2 H, Ar—H], 8.33 [s, 1 H, NH], 8.47 [s, 1 H, Ar—H], 8.66 [s, 1 H, Ar—H]. $^{13}$C NMR (DCCl$_3$) ppm 26.28 [CH$_2$], 30.44 [CH$_3$], 30.67 [CH$_3$], 36.42 [OCH$_2$], 50.70 [C(CH$_3$)$_2$], 64.27 [COCH$_3$], and Ar—C [122.47, 122.74, 125.00, 125.09, 125.41, 129.28, 132.73, 143.77, 144.46, 149.86], 178.68 [C=S], and 197.16 [C=O]. Calcd for C$_{20}$H$_{21}$N$_3$O$_4$S: C, 60.13; H, 5.30; N, 10.52; S, 8.03. Calcd for C$_{20}$H$_{21}$N$_3$O$_4$S.0.5 H$_2$O: C, 58.81; H, 5.43; N, 10.29; S, 7.85. Found: C, 59.07; H, 5.58; N, 10.13; S, 7.72.

EXAMPLE X 2,2,4,4-Tetramethyl-6-(2-propylamino)thiochroman (47), [{Methylethyl)(2,2,4,4,7-pentamethyl-(3H-benzo[3,4-e]thian-6-yl)}amino][(4-nitrophenyl) amino]methane]-1-thione (48), and Ethyl 4-{[N-Methylethyl)-N-(2,2,4,4-tetramethyl(3H-benzo[3,4-e]thian-6-yl))carbamoyl]amino}benzoate (49)

A mixture of 6 (1.50 g, 6.78 mmol), dry acetone (0.589 g, 10.16 mmol), titanium IV isopropoxide (1.93 g, 6.78 mmol), and ethanol (6 mL) was stirred for 18 h. To the yellow mixture was added portionwise sodium cyanoborohydride (8.51 g, 13.5 mmol) over 3 min, and the resulting mixture was stirred for 12 h. After cooling to 0° C., the reaction was quenched with aqueous ammonia (2 N, ~15 mL), and the solid was filtered out. The solvent was evaporated to an oil which was partitioned between water and ether (3×40 mL). The combined organics were washed with brine and dried (Na$_2$SO$_4$). Evaporation of the solvent gave an oil which was subjected to flash chromatography over silica gel with hexanes:EtOAc (10:1) and yielded a thick red oil 47 (1.5 g, 67%). IR (neat) 3395 (N—H) cm$^{-1}$; $^1$H NMR (DCCl$_3$) δ 1.20 [d, 6 H, J=6.3 Hz, NC(CH$_3$)$_2$], 1.36 [s, 6 H, C(CH$_3$)$_2$], 1.38 [s, 6 H, C(CH$_3$)$_2$] 1.89 [s, 2 H, CH$_2$], 3.30 [s, 1 H, NH], 3.58 [q, 1 H, J=6.3 Hz, CH], 6.38 [q, 1 H, Ar—H], 6.65 [d, 1 H, Ar—H], 6.94 [d, 1 H, Ar—H]. This sample of 47 was used immediately to prepare 48 and 49.

A solution of 47 (0.410 g, 1.56 mmol) in THF (6 mL) was treated dropwise with 4-nitrophenylisothiocyanate (0.309 g, 1.71 mmol) in THF (11 mL) at 0–5° C. under N$_2$. The reaction mixture was allowed to warm to room temperature and was then stirred overnight. Evaporation of the solvent gave a light yellow solid which was recrystallized (pentane:H$_2$CCl$_2$, 4:1) to yield 48 (0.330 g, 48%) as a yellow solid, mp 142–143° C. IR (KBr) 3366 (N—H) cm$^{-1}$; $^1$H NMR (DCCl$_3$) δ 1.15 [d, 6 H, J=6.7 Hz, NC(CH$_3$)$_2$], 1.41 [s, 6 H, CC(CH$_3$)$_2$], 1.47 [s, 6 H, CC(CH$_3$)$_2$], 2.01 [s, 2 H, $CH_2$], 5.92 [m, 1 H, NCH], 6.90 [m, 1 H, Ar—H], 7.06 [s, 1 H, NH], 7.18 [s, 1 H, Ar—H], 7.28 [d, 1 H, Ar—H], 7.56 [m, 2 H, Ar—H], 8.13 [m, 2 H, Ar—H]; $^{13}$C NMR (DCCl$_3$) ppm 20.87, 31.50, 32.72, 35.60, 42.42, 51.81, 53.43, and Ar—C [123.8, 124.0, 126.8, 128.1, 129.4, 132.7, 135.6, 144.1, 144.9, 145.0], and 179.41 [C=S]. Calcd for $C_{23}H_{29}N_3O_2S_2$: C, 62.27; H, 6.59; N, 9.47; S, 14.46. Found: C, 62.32; H, 6.64; N, 9.49; S, 14.42.

A solution of 47 (0.500 g, 1.90 mmol) in THF (11 mL) was treated dropwise with ethyl 4-isocyanatobenzoate (0.400 g, 2.09 mmol) in THF (10 mL) at 0–5° C. under $N_2$. The reaction mixture was allowed to warm to room temperature and was then stirred overnight. Removal of the solvent afforded a white solid which was recrystallized (pentane:$CH_2Cl_2$, 8:1) to give 49 (0.290 g, 34%) as a white solid, mp 92–93° C. IR (KBr) 3388 (N—H), 1708 (C=O), 1680 cm$^{-1}$; $^1$H NMR δ 1.10 [d, 6 H. J=6.7 Hz, NC(CH$_3$)$_2$], 1.39 [m, 9 H, C(CH$_3$)$_2$ and CH$_2$CH$_3$], 1.48 [s, 6 H, C(CH$_3$)$_2$], 2.01 [s, 2 H, CH$_2$], 4.32 [q, 2 H, J=7.1 Hz, OCH$_2$], 4.92 m, 1 H, J=6.9 Hz NCH], 6.20 [s, 1 H, NH], 6.93 [m, 1 H, Ar—H], 7.22 [m, 2 H, Ar—H], 7.30 [m, 2 H, Ar—H], 7.90 [m, 2 H, Ar—H]; $^{13}$C NMR (DCCl$_3$) ppm 14.32, 21.40, 31.52, 32.73, 35.51, 42.31, 46.65, 53.63, 60.61, and Ar—C [117.8, 124.2, 128.1, 129.1, 129.4, 130.6, 133.2, 134.3, 143.3, 144.4], 153.5 [NCONH], and 166.3 [C=O]. Calcd for $C_{26}H_{34}N_2O_3S$: C, 68.69; H, 7.54; N, 6.16; S, 7.05. Found: C, 68.84; H, 7.76; N, 6.11; S, 6.78.

EXAMPLE XI

As a representative example of a compound related to those in Example X, but initiating from 29 rather than from 6, we illustrate the synthesis of 51 via 29→50→51.

A solution of the amine 29 (1.0 g, 4.25 mmol), acetone (0.37 g, 6.37 mmol), titanium (VI) isopropoxide (Aldrich, 1.20 g, 4.25 mmol), and ethanol (4 mL) was stirred for 24 h. To the resulting yellow solution was added sodium cyanoborohydride (0.534 g, 8.50 mmol) portionwise over 10 min, and the resulting solution was stirred for 24 h. The flask was cooled to 0° C., and the reaction was quenched with aqueous ammonia (10 mL, 2 N). The resulting inorganic precipitate was filtered and washed with ether. The filtrate was then concentrated in vacuo, cooled (8° C.), and refiltered. The aqueous layer was extracted with ether (3×30 mL). The combined organic layers were washed with brine and then dried (Na$_2$SO$_4$). Evaporation of the solvent in vacuo gave amine 50 as a light yellow oil. Crystallization followed, and then recrystallization (H$_3$C—OH) and standing in a freezer gave 50 (0.900 g, 76%) as a white solid, mp 90–92° C. IR (KBr) 3385 (N—H), cm$^{-1}$; $^1$H NMR (DCCl$_3$) δ 1.22 [d, 6 H, J=6.3 Hz, NC(CH$_3$)$_2$], 1.23 [s, 6 H, C(CH$_3$)$_2$], 1.51 [s, 6 H, C(CH$_3$)$_2$], 3.55 [m, 1 H, NCH], 3.59 [s, 2 H, CH$_2$], 3.83 [s, 3 H, OCH$_3$], 3.92 [s, 1 H, NH], 6.22 [s, 1 H, Ar—H], 6.63 [s, 1 H, Ar—H]; $^{13}$C NMR (DCCl$_3$) ppm 22.96, 27.07, 29.82, 33.31, 43.78, 55.31, 71.23, 75.03, and Ar—C[105.7, 106.7, 129.6, 133.7, 135.2, 145.4]. The intermediate 50 was used immediately and without further purification for the preparation of 51.

To a solution of amine 50 (0.400 g, 1.44 mmol) in THF (8 mL) was added dropwise 4-nitrophenylisothiocyanate (0.286 g, 1.59 mmol) in THF (10 mL) at –5° C. under $N_2$. The reaction mixture was allowed to warm to room temperature and was then stirred overnight. Evaporation of the solvent afforded an yellow oil which crystallized upon standing and was recrystallized [pentane:$CH_2Cl_2$, 5:1] to give 51 (0.300 g, 45%) as a light yellow solid, mp 176° C. (dec). IR (KBr) 3374 (N—H), cm$^{-1}$; $^1$H NMR (DCCl$_3$) δ 1.00 [d, 3 H, J=6.7 Hz, NCCH$_3$], 1.23 [d, 3 H, J=6.5 9 Hz, NCCH$_3$], 1.32 [s, 6 H, C(CH$_3$)$_2$], 1.53 [s, 6 H, C(CH$_3$)$_2$], 3.63 [s, 2 H, CH$_2$], 3.84 [s, 3 H, OCH$_3$], 5.86 [m, 1 H, NCH], 6.84 [s, 1 H, Ar—H(5)], 6.95[s, 1 H, Ar—H(8)], 7.05 [s, 1 H, NH], 7.53 [d, 2 H, J=9.1 Hz, Ar—H(13), Ar—H(17)], 8.24 [s, 2 H, J=9.1 Hz, Ar—H(14), Ar—H(16)]; $^{13}$C NMR (DCCl$_3$) ppm 19.23, 21.44, 26.83, 26.91, 29.62, 29.83, 34.37, 52.70, 55.57, 70.44, 74.54, and Ar—C [108.9, 122.7, 123.9, 124.2, 127.3, 135.3, 144.0, 145.4, 146.0] 153.7, and 180.1 [C=S]. Calcd for $C_{24}H_{31}N_3O_4S$: C, 63.00; H, 6.83; N, 9.18; S, 7.01. Found: C, 62.78; H, 6.94; N, 9.06; S, 6.91.

EXPERIMENTAL PROCEDURES AND RESULTS

The following explanation of experimental procedures used to evaluate the compounds of the present invention and the results obtained therefrom serve to further illustrate the invention and the utility of the inventive compounds.

General Method for Growth Inhibition Assay

To illustrate the general and useful biological activity of the heteroarotinoids described in this invention, selected compounds were screened for ability to inhibit the growth of three ovarian cancerous cell lines, namely Caov, SKOV, and OVCAR cell lines, three cervical cell lines (Cervix HPV-Wt p53, Cervix HPV-Mut p53, and Cervix HPV-Mut p53), and one vulvar (Vulvar HPV-Mut p53) cell line as shown in Tables I–III. The cell lines and the technology have been previously described [See Journal of Medicinal Chemistry, 1999, Vol. 42, pages 3602–3614 in an article entitled "Synthesis, Structure-Activity Relationships, and RAR γ-Ligand Interactions of Nitrogen Heteroarotinoids" by A. Dhar, S. Liu, J. Klucik, K. D. Berlin, M. M. Madler, S. Lu, R. T. Ivey, D. Zacheis, C. W. Brown, E. C. Nelson, P. J. Birckbichler, and D. M. Benbrook], but the general technique was slightly modified. Cultures of the cancerous cells were plated in volumes of 150 μL in 96-well microtiter plates at concentrations of 2000–4000 cells/well, depending upon the cell line used. Retinoids were added the next day at 4× the concentrations in 50 μL of media resulting in 1, 2, 3, 4, 5, 7, and 10 μM final concentrations of each retinoid. Control cultures were treated with the same volume of DMSO. After 3 days of treatment, the cell density in each well was determined by fixing the cells in trichloroacetic acid followed by staining the cytoplasmic proteins with sulforhoamine B (SRB). After rinsing, the SRB was solubilized in Tris-HCl, and the optical density of each culture was determined with a MR600 microtiter plate reader. Each experiment was performed in triplicate, and the three values of each treatment were averaged. The average OD of the treated cultures was divided by that of the control cultures treated with solvent alone. To determine the percent growth inhibition, this ratio was subtracted from 1 and multiplied by 100. Tables I, II, and III contain representative examples of the inhibition of growth by the inventive heteroarotinoids of the cancerous cell lines investigated at two independent concentrations (1 and 10 μM). As standards for comparison purposes, trans-retinoic acid (t-RA), 9-cis-retinoic acid (9-c-RA), 13-cis-retinoic acid (13-c-RA), and 4-hydroxyretinamide (4-HPR) were added in parallel experiments along with the heteroarotinoids and with dimethyl sulfoxide (DMSO) as the solvent. For convenience, the data in Tables II and III are duplicated and ranked according to tumor type.

TABLE I

PERCENTAGE GROWTH INHIBITION INDUCED BY A THREE-DAY TREATMENT OF SEVEN CANCEROUS CELL LINES WITH 10 $\mu$M HETEROARTOTINOIDS COMPARED TO 9-c-RA

| Cell Type<br>Cell Line | Cervix<br>HPV+<br>Wt p53<br>SiHa | Cervix<br>HPV–<br>Mut p53<br>HT-3 | Cervix<br>HPV–<br>Mut p53<br>C-33A | Vulva<br>HPV–<br>Mut p53<br>SW962 | Ovarian<br>HPV–<br>Mut p53<br>CAOV-3 | Ovarian<br>HPV–<br>Mut p53<br>OVCAR-3 | Ovarian<br>HPV–<br>Null p53<br>SK-OV-3 |
|---|---|---|---|---|---|---|---|
| Agent | | | | | | | |
| 11 | 72 | 82 | 87 | 98 | 80 | 94 | 100 |
| 12 | 62 | 65 | 84 | 95 | 95 | 74 | 90 |
| 13 | 66 | 85 | 76 | 96 | 98 | 77 | 94 |
| 9-c-RA | 24 | 47 | 44 | 31 | 27 | 28 | 30 |

TABLE II

PERCENTAGE OF GROWTH INHIBITION BY HETEROAROTINOIDS WITH THREE-ATOM LINKERS IN THREE CELL LINES AT 1 MICROMOLAR CONCENTRATION
1 $\mu$M CONCENTRATION OF THE HETEROAROTINOID

| | Ranked by CAOV-3 | | | | Ranked by SK-OV-3 | | | | Ranked by OVCAR-3 | | |
|---|---|---|---|---|---|---|---|---|---|---|---|
| HET | CAOV-3 | SKOV-3 | OVCAR-3 | HET | CAOV-3 | SKOV-3 | OVCAR-3 | HET | CAOV-3 | SKOV-3 | OVCAR-3 |
| 15 | 19.85 | −1.86 | 8.91 | 13-c-RA | | 28.5 | 9.8 | 40 | 15.24 | 1.82 | 15.47 |
| 24 | 17.55 | 1.86 | −2.16 | 9-c-RA | | 23.0 | 6.2 | 39 | 14.39 | 3.60 | 14.37 |
| 16 | 15.33 | −1.67 | 10.20 | 34 | | 22.2 | 2.2 | 21 | | 9.5 | 12.1 |
| 40 | 15.24 | 1.82 | 15.47 | 19 | | 16.3 | 9.6 | 20 | | 14.7 | 10.3 |
| 39 | 14.39 | 3.60 | 14.37 | 20 | | 14.7 | 10.3 | 16 | 15.33 | −1.67 | 10.20 |
| 23 | 11.36 | −0.79 | −0.19 | 18 | | 10.5 | 10.1 | 18 | | 10.5 | 10.1 |
| 32 | 9.88 | −1.99 | 4.31 | 35 | | 10.3 | 5.6 | 13-c-RA | | 28.5 | 9.8 |
| 38 | 8.79 | −2.39 | 9.48 | 36 | | 10.2 | 8.0 | 19 | | 16.3 | 9.6 |
| 41 | 7.58 | −2.72 | 7.18 | 21 | | 9.5 | 12.2 | 38 | 8.79 | −2.39 | 9.48 |
| 45 | 7.18 | −4.18 | 9.20 | t-RA | | 8.8 | 6.0 | 45 | 7.18 | −4.18 | 9.20 |
| 31 | 6.88 | −1.42 | 3.83 | 4-HPR | | 7.2 | 2.7 | 15 | 19.85 | −1.86 | 8.91 |
| 46 | 3.85 | −1.53 | 8.57 | 39 | 14.39 | 3.60 | 14.37 | 33 | 3.79 | 1.65 | 8.81 |
| 33 | 3.79 | 1.65 | 8.81 | 14 | −4.00 | 3.58 | −6.70 | 46 | 3.85 | −1.53 | 8.57 |
| DMSO | 0.03 | 0.08 | −0.10 | 17 | | 3.0 | 6.6 | 36 | | 10.2 | 8.0 |
| 14 | −4.00 | 3.58 | −6.70 | 24 | 17.55 | 1.86 | −2.16 | 41 | 7.58 | −2.72 | 7.18 |
| 22 | −9.97 | 1.09 | 4.07 | 40 | 15.24 | 1.82 | 15.47 | 17 | | 3.0 | 6.6 |
| 21 | | 9.5 | 12.1 | 33 | 3.79 | 1.65 | 8.81 | 9-c-RA | | 23.0 | 6.2 |
| 20 | | 14.7 | 10.3 | 22 | −9.97 | 1.09 | 4.07 | t RA | | 8.8 | 6.0 |
| 18 | | 10.5 | 10.1 | DMSO | 0.03 | 0.08 | −0.10 | 35 | | 10.3 | 5.6 |
| 13-c-RA | | 28.5 | 9.8 | 23 | 11.36 | −0.79 | −0.19 | 32 | 9.88 | −1.99 | 4.31 |
| 19 | | 16.3 | 9.6 | 31 | 6.88 | −1.42 | 3.83 | 22 | −9.97 | 1.09 | 4.07 |
| 36 | | 10.2 | 8.0 | 46 | 3.85 | −1.53 | 8.57 | 31 | 6.88 | −1.42 | 3.88 |
| 17 | | 3.0 | 6.6 | 16 | 15.33 | −1.67 | 10.20 | 4-HPR | | 7.2 | 2.7 |
| 9-c-RA | | 23.0 | 6.2 | 15 | 19.85 | −1.86 | 8.91 | 34 | | 22.2 | 2.2 |
| t-RA | | 8.8 | 6.0 | 32 | 9.88 | −1.99 | 4.31 | DMSO | 0.03 | 0.08 | −0.10 |
| 35 | | 10.3 | 5.6 | 38 | 8.79 | −2.39 | 9.48 | 23 | 11.36 | −0.79 | −0.19 |
| 4-HPR | | 7.2 | 2.7 | 41 | 7.58 | −2.72 | 7.18 | 24 | 17.55 | 1.86 | −2.16 |
| 34 | | 22.2 | 2.2 | 45 | 7.18 | −4.18 | 9.20 | 14 | −4.00 | 3.58 | −6.70 | t-RA = trans-retinoic acid;
9-c-RA = 9-cis-retinoic acid;
13-c-RA = 13-cis-retinoic acid;
4-HPR = 4-hydroxyphenylretinamide;
DMSO = dimethyl sulfoxide

TABLE III

PERCENTAGE OF GROWTH INHIBITION BY HETEROAROTINOIDS WITH THREE-ATOM LINKERS IN THREE CELL LINES AT 1 MICROMOLAR CONCENTRATION
10 $\mu$M CONCENTRATION OF THE HETEROAROTINOID

| | Ranked by CAOV-3 | | | | Ranked by SK-OV-3 | | | | Ranked by OVCAR-3 | | |
|---|---|---|---|---|---|---|---|---|---|---|---|
| HET | CAOV-3 | SKOV-3 | OVCAR-3 | HET | CAOV-3 | SKOV-3 | OVCAR-3 | HET | CAOV-3 | SKOV-3 | OVCAR-3 |
| 22 | | | 40.14 | 22 | | | 40.14 | 41 | 61.94 | 45.45 | 81.71 |
| 16 | 83.22 | 52.81 | 74.05 | 17 | | 65.3 | 64.9 | 31 | 30.81 | 27.41 | 80.59 |

TABLE III-continued

PERCENTAGE OF GROWTH INHIBITION BY HETEROAROTINOIDS WITH THREE-ATOM LINKERS IN THREE CELL LINES AT 1 MICROMOLAR CONCENTRATION
10 μM CONCENTRATION OF THE HETEROAROTINOID

| | Ranked by CAOV-3 | | | | Ranked by SK-OV-3 | | | | Ranked by OVCAR-3 | | |
|---|---|---|---|---|---|---|---|---|---|---|---|
| HET | CAOV-3 | SKOV-3 | OVCAR-3 | HET | CAOV-3 | SKOV-3 | OVCAR-3 | HET | CAOV-3 | SKOV-3 | OVCAR-3 |
| 41 | 61.94 | 45.45 | 81.71 | 4-HPR | | 64.9 | 43.1 | 16 | 83.22 | 52.81 | 74.05 |
| 24 | 53.11 | 7.98 | 26.53 | 16 | 83.22 | 52.81 | 74.05 | 17 | | 65.3 | 64.9 |
| 45 | 42.75 | 20.02 | 47.25 | 41 | 61.94 | 45.45 | 81.71 | 33 | 40.04 | 15.60 | 52.61 |
| 33 | 40.04 | 15.60 | 52.61 | 19 | | 33.3 | 33.2 | 45 | 42.75 | 20.02 | 47.25 |
| 40 | 37.84 | 9.27 | 33.74 | 31 | 30.81 | 27.41 | 80.59 | 20 | | 12.1 | 47.1 |
| 31 | 30.81 | 27.41 | 80.59 | 45 | 42.75 | 20.02 | 47.25 | 46 | −5.35 | 0.25 | 43.15 |
| 23 | 17.77 | 7.67 | 2.75 | 9-c-RA | | 16.0 | 5.3 | 4-HPR | | 64.9 | 43.1 |
| 32 | 16.30 | −5.01 | 18.33 | 33 | 40.04 | 15.60 | 52.61 | 15 | −9.56 | 9.83 | 40.90 |
| 14 | 6.12 | 0.43 | 5.45 | 20 | | 12.1 | 47.1 | 22 | | | 40.13 |
| DMSO | −0.04 | 0.06 | 0.00 | 15 | −9.56 | 9.83 | 40.90 | 40 | 37.84 | 9.27 | 33.74 |
| 46 | −5.35 | 0.25 | 43.15 | 40 | 37.84 | 9.27 | 33.74 | 19 | | 33.3 | 33.2 |
| 15 | −9.56 | 9.83 | 40.90 | 18 | | 8.5 | 18.7 | 24 | 53.11 | 7.98 | 26.53 |
| 39 | −14.65 | −10.01 | 15.45 | 24 | 53.11 | 7.98 | 26.53 | 21 | | −13.9 | 19.5 |
| 38 | −16.12 | −7.70 | 8.96 | 23 | 17.77 | 7.67 | 2.75 | 18 | | 8.5 | 18.7 |
| 17 | | 65.3 | 64.9 | t-RA | | 6.0 | −3.0 | 32 | 16.3 | −5.01 | 18.33 |
| 20 | | 12.1 | 47.1 | 34 | | 6.0 | 30.5 | 39 | −14.65 | −10.01 | 15.45 |
| 4-HPR | | 64.9 | 43.1 | 14 | 6.12 | 0.43 | 5.45 | 38 | −16.12 | −7.70 | 8.96 |
| 19 | | 33.3 | 33.2 | 46 | −5.35 | 0.25 | 43.15 | 35 | | −14.3 | 6.1 |
| 21 | | −13.9 | 19.5 | DMSO | −0.04 | 0.06 | 0.00 | 14 | 6.12 | 0.43 | 5.45 |
| 18 | | 8.5 | 18.7 | 36 | | −3.1 | 4.7 | 9-c-RA | | 16.0 | 5.3 |
| 35 | | −14.3 | 6.1 | 32 | 16.30 | −5.01 | 18.33 | 36 | | −3.1 | 4.7 |
| 9-c-RA | | 16.0 | 5.3 | 38 | −16.12 | −7.70 | 8.96 | 23 | 17.77 | 7.67 | 2.75 |
| 36 | | −3.1 | 4.7 | 39 | −14.65 | −10.01 | 15.45 | DMSO | −0.04 | 0.06 | 0.00 |
| t-RA | | 6.0 | −3.0 | 21 | | −13.9 | 19.5 | t-RA | | 6.0 | 3.0 |
| | | | | 35 | | −14.3 | 6.1 | | | | | t-RA = trans-retinoic acid;
9-c-RA = 9-cis-retinoic acid;
13-c-RA = 13-cis-retinoic acid;
4-HPR = 4-hydroxyphenylretinamide;
DMSO = dimethyl sulfoxide The overall applicability of the heteroarotinoids is demonstrated against the variety of tumor types with different genetic defects (Table I). The majority of cervix tumors contain Human Papillomavirus (HPV) DNA, and heteroarotinoids 11, 12, and 13 were active against cell lines regardless of the presence (HPV+) or absence (HPV−) of HPV (Table I). The majority of tumors of any type contain p53 mutations, and heteroarotinoids 11, 12, 13 were quite active against both cell lines containing normal (Wt p53) and mutant (Mut p53) cells.

It is clear that there is a gradient of activity with respect to the inhibitory ability of growth of the cell lines by the various heteroarotinoids (Tables I–III). There is also a difference observed in terms of inhibition at the two different concentrations of agents employed (Tables II and III). The changes in substituents within the structures could not have been predicted to elicit the activity displayed by the heteroarotinoids. It is also remarkable that the activity shown by a significant number of these heteroarotinoids exceeded the activity of the controls, all of which have been and are still used in clinics. For example, at the 1 μM concentration (Table II) the inhibition of growth of the OVCAR cell line by heteroarotinoid 40 exceeded that of 13-c-RA by about 40%, that of 9-c-RA by about 120%, that of t-RA by about 120%, and that of 4-HPR by more than 1200%. Thus, the heteroarotinoids are proved active in inhibiting the growth of the exemplar cell lines.

Apoptosis Assay

The greater than 74% of growth inhibition in the OVCAR-3 cell line in the three-day treatment experiment (Table I) indicated that cell loss occurred in the cultures treated with heteroarotinoids 11–13. Optimal chemotherapeutic agents will selectively kill tumor cells by inducing a natural form of cell death which is called "apoptosis". Toxic agents kill both normal and tumor cells via a nonspecific process known as "necrosis". To differentiate between apoptosis and necrosis in heteroarotinoid-treated cultures, a flow cytometric assay was employed. Treated cultures were stained with Annexin-V-Flous and propidium iodide, and the intensities of the stains are quantitated with Flow Cytometry. The Annexin-V-Flous binds to phosphatidyl serine on the exterior of apoptosing cells. This assay is specific for apoptosing cells because phosphatidyl serine is normally located on the inner membrane of the cells, a situation whereby the serine derivative cannot be bound by Annexin. However, during apoptosis, phosphatidyl serine is translocated to the outer membrane. The Flous moiety emits a signal that can be detected and quantitated by Flow Cytometry. In contrast, propidium iodide is taken up by necrotic cells that have lost membrane integrity. In this study, t-RA was used as a control for the non-apoptotic retinoids, and 4-HPR was used as a control for the apoptotic retinoids. The results are shown in Table IV.

TABLE IV

PERCENTAGE OF INDUCTION OF APOPTOSIS IN SW962
VULVAR CARCINOMA CULTURES BY AGENT 11 AND 4-HPR
BUT NOT t-RA

| Compound Days | 11 | 4-HPR | t-RA |
| --- | --- | --- | --- |
| 0 | 3 | 3 | 3 |
| 1 | 6.11 | 1.67 | 2.53 |
| 2 | 11.42 | 3.6 | — |
| 3 | 39.06 | 17.28 | 1.25 |
| 4 | 48.79 | — | 4.5 |
| 7 | 47.5 | — | 3.51 |

In another experiment, the ovarian carcinoma cell line OVCAR-3 was grown in organotypic culture. After one week, the cultures were treated with 1 µM solution of heteroarotinoids 11, 12, and 13, or with the same volume of DMSO (solvent), for two weeks. Both 9-c-RA and 4-HPR were used as controls. At the end of the time, the cultures were fixed in sectioned, and stained with the TUNNEL assay to detect apoptosing cells. An experienced pathologist quantitated the percent of apoptosing cells by light microscopic examination. The results are shown in Table V.

TABLE V

PERCENTAGE OF APOPTOSING OF OVCAR-3 CELLS WITH HETEROAROTINOIDS

| AGENT | % APOPTOSIS |
| --- | --- |
| 4-HPR | 95 |
| DMSO (control) | 10 |
| 9-c-RA | 80 |
| 11 | 95 |
| 12 | 75 |
| 13 | 80 |

4-HPR = 4-hydroxyphenylretinamide;
9-c-RA = 9-cis-retinoic acid.

Apoptosis, or cell death, was observed in selected heteroarotinods that exhibited the strongest inhibition of growth in the cancerous cell lines included in Tables II and III. Thus, the percentages of cells which underwent apoptosis in treated cultures correlated significantly with growth inhibition (R=0.9749, p=0.0017). Representative agents 11, 12, and 13 were chosen for more detailed apoptosis studies (Tables IV and V). It is clear that agent 11 in the SW962 vulvar cell (Table IV) was superior to the clinically used agent 4-HPR in the apoptosis experiment and exceeded the value for the common standard t-RA. With the OVCAR-3 cell line (Table V), both 11 and 13 were as effective as 4-HPR while 12 was only slightly less effective in inducing apoptosis. Thus, the heteroarotinoids possess a range of abilities to induce apoptosis of these cancerous cells.

In Vivo Tumor Xenographs

To demonstrate biological activity in vivo, an ovarian xenograph mouse model was employed. Thirty female athymic nu/nu mice (Charles Rivers Laboratories, Wilmington, Mass.) were housed in a laminar flow room under sterile conditions at 83–85° F. The mice were quarantined for one week prior to the beginning of the study and were allowed access to autoclaved food (Purina 5001 mouse/rat sterilized diet, St. Louis, Mo.) and water ad libitum. Then OVCAR-3 cells in log phase growth were harvested by trypsinization, resuspended in RPMI culture medium, and centrifuged at 3000 rpm for 10 min. The pellets were then resuspended in RPMI culture medium at a concentration of $7 \times 10^6$ cells/mL before implantation into mice. Animals were injected with $3.5 \times 10^6$ cells into right scapular region with a 24-gauge needle/1 mL tuberculin syringe (Becton Dickinson, Rutherford, N.J.). Twenty four hours after tumor implantation, animals were randomized into four treatment groups of 5 animals each. Retinoids were administered daily p.o. beginning 35 days after tumor implantation with a 20-gauge intragastric feeding tube (Popper & Sons, New Hyde Park, N.Y.), 5 days/week, at doses of 10 mg/kg/day in 0.1 mL of super refined sesame oil (Corda, Inc., Parisppany, N.J.). Tumors were measured with calipers weekly, and tumor volumes were calculated using the formula: volume= length×width×heigth. Animal weights and clinical signs of overall health status and cutaneous toxicities were recorded weekly. Agents 11 and 13 were evaluated against the 4-HPR standard. FIG. 1 illustrates the overall changes in tumor volumes found in the mice in these experiments. As can be seen in FIG. 1, both 11 and 13 inhibited tumor growth to similar extents. After 15 days of treatment, the sizes of the tumors in the animal group treated with 11 and 13 were significantly smaller than in the control group treated with sesame oil alone (t-test: P<0.05). The animals were monitored daily for signs of toxicity, such as skin eczema and bone fractures, but none were observed. This is added evidence that these heteroarotinoids are strong candidates for cancer chemotherapy.

Liver Toxicity

Although no skin or bone toxicity signs were seen in the mice employed in the study, some retinoids are known to cause liver toxicity which requires laboratory assays to quantify [See "Adverse Effects of Retinoids" in Medical Toxicolgy Adverse Drug Exp., volume 3, 1988, pp 213–219, by M. David, E. Hodak, and N. J. Lowe]. Toxic compounds can induce livers to release enzymes called serum transaminases, such as alanine aminotransferase (ALT). The assay for ALT is the most universally accepted clinical laboratory marker used to evaluate hepatic toxicity induced by pharmaceuticals [See "Serum Transferase Elevations as Indicators or Hepatic Injury Following the Administration of Drugs", Reg. Tox. Pharm., volume 27, 1998, pp 119–130, by D. E. Amacher]. At the end of the treatment period, blood was drawn from each animal. Plasma was separated by centrifugation and stored at −70° C. The activity of ALT was determined in aliquots of plasma by standard spectrophotometric enzymatic techniques which were based upon the reduction of pyruvate by lactate dehydrogenase [See "Aged Mice are Resistant to the Hepatotoxic Effects of Endotoxin and Galactosamine" in Exp. Mol. Pathology, volume 59, 1993, pp 27–37]. The method measures the disappearance of NADH from time of incubation at 37° C. The activities have been expressed in µm/Liter/min (Table VI). Two different amounts of plasma were utilized in each assay to assure the measurement of the maximum rate. Eleven mice in the control and treated groups exhibited ALT activities that were in the normal range of 28 to 184 µL/min as determined by the commercial suppliers of the mice (Charles River Laboratories, Wilmington, Mass.).

TABLE VI

ALT ACTIVITY IN PLASMA OF MICE TREATED WITH 11, 13, 4-HPR, and SESAME OIL

| TREATMENT | ALT ACTIVITY (µm/Liter/Min) |
| --- | --- |
| 11 | 118.5 ± 153.4 |
| 12 | 64.5 ± 40.3 |

TABLE VI-continued

ALT ACTIVITY IN PLASMA OF MICE TREATED WITH 11, 13, 4-HPR, and SESAME OIL

| TREATMENT | ALT ACTIVITY (μm/Liter/Min) |
|---|---|
| 4-HPR | 149.7 ± 140.9 |
| SESAME OIL | 103.0 ± 60.3 |

There were no statistically significant differences between the ALT activities in the different treatment groups (Table VI, t-test: P>0.05). All numbers were in the normal range (63 to 307 μm/Liter/Min) of ALT values for the species of mouse utilized. All liver sections were assessed by an experienced pathologist in a blinded manner. The degree of necrosis was very mild in all animals. Thus, the heteroarotinoids 11 and 13, as well as 4-HPR, do not appear to induce significant liver toxicity.

Receptor Activation

Both heteroarotinoids 11 and 13 resemble 4-HPR in that all are potent inducers of apoptosis. Since 4-HPR acts through a receptor-independent mechanism, agent 11 was evaluated for ability to transactivate a RARE reporter through endogenous receptors in the SW962 vulvar carcinoma cell line. The general method has been described [See "Biologically Active Heteroarotinoids Exhibit Anticancer Activity and Decreased Toxicity", Journal of Medicinal Chemistry Volume 40, 1997, pp 3576–3583, by D. M. Benbrook, M. M. Madler, L. W. Spruce, P. J. Birckbichler, E. C. Nelson, S. Subramanian, G. M. Weerasekare, J. B. Gale, M. K. Patterson, Jr., B. Wang, W. Wang, S. Lu, T. C. Rowland, P. DiSivestro, C. Lindamood, D. L. Hill, and K. D. Berlin]. No induction of the retinoid receptors was observed although 9-cis-RA casued a 4 to 10 fold induction of RARE-driven transcription in the same experiment with the SW962 cell line. To further demonstrate the lack of transactivation, 11 was again assessed for ability to activate each of the retinoic acid receptors in a CV-1 co-transfection assay. No transactivation was observed in these experiments in which 9-cis-RA did demonstrate a 2 to 4 fold induction. Thus, these heteroarotinoids do not appear: to activate the common retinoid receptors.

Statistical Analysis

All data were entered into Microsoft Excel 5.0, which was used to perform t-tests and to derive correlation coefficients.

Thus, it may be appreciated that heteroarotinoids 11 and 13, administered at the maximum tolerated dose (MTD) for t-RA (10 mg/kg/day), decreased xenograph tumor growth and did not cause toxicity to the skin, bones, or liver. These results, and the other results discussed above, clearly demonstrate that the heteroarotinoids described herein are as effective as the current retinoid standard 4-HPR for ovarian cancer chemoprevention. The inventive compounds appear to have advantages over the current retinoid standards insofar as they demonstrate the ability to induce apoptosis at clinically achievable concentrations. Current understanding of retinoid chemoprevention mechanisms is complicated by the finding that promising compounds, such as 4-HPR, induce apoptosis through retinoic acid receptor-independent mechanisms only at concentrations above those achieved in clinical chemoprevention trials. At lower concentrations ($\leq 1$ μM) however, 4-HPR acts similar to classical retinoids by inducing differentiation through a receptor-dependent mechanism. Comparison of the inventive heteroarotinoid structures with their biologic activities revealed that the compounds containing more flexible connecting ester linkages were unable to induce apoptosis. In contrast, all of the compounds capable of inducing apoptosis contained the more rigid three atom linkers. The more rigid apoptotic hetereroarotinoids appear to hold greater promise as chemoprevention agents, since they induce similar levels of growth inhibition as the growth inhibitory retinoids, while inducing significantly greater levels of apoptosis. The fact that the inventive heteroarotinoids and known heteroarotinoids induce similar levels of growth inhibition indicates that the new compounds are significantly improved over prior compounds in that they retain the same anti-cancer activities (i.e. growth inhibition and induction of differentiation) while exhibiting additional more potent anti-cancer activities (i.e. apoptosis).

Furthermore, the inventive heteroarotinoids are significantly different than previously described heteroarotinoids in that they act in a receptor-independent mechanism, while prior known compounds activated the retinoid receptors.

Chemosensitization

The compounds of the present invention also find advantage over the standard retinoids, including retinoic acid and 4-HPR as chemosensitization agents. In another study, ovarian carcinoma cultures, including cisplatin-resistant cultures, were trypsinized and plated in microtiter plates at a concentration of 1000 cells per well. A series of natural and synthetic retinoids, including exemplar heteroarotinoids with the novel three atom linker, at a concentration of 5 μM were added to triplicate wells in the microtiter plates twenty-four hours later. The same volume of DMSO used to administer the compounds were added to the control cultures. After three days of treatment, a range of cisplatin concentrations were added to the wells. After one hours of exposure, the media and retinoid drugs were replenished. Cell survival was quantitated using the MTS assay (Promega). It was found that cisplatin-resistant cultures were sensitized and that the synthetic heteroarotinoids were more effective than retinoic acid and 4-HPR. Thus, the present invention contemplates the process of sensitizing cells to cisplatin therapy and combined cisplatin and radiation therapy using the inventive heteroarotinoids.

Once the results were obtained that 5 micromolar concentrations of 4-HPR and heteroarotinoids prevented the growth increase induced by a range of cisplatin concentrations in the OVCAR-3 cisplatin-resistant ovarian carcinoma cell line, a further experiment was conducted to determine whether the inventive compounds were better than the industry standard 4-HPR at the clinically achievable concentration of 1 micromolar. In this regard, the cisplatin resistant OVCAR-3 cell line was pre-treated with a concentration of 1 μM of the indicated retinoids for 3 days, and then exposed to cisplatin at the concentration detected in tumors of treated patients (40 μM or 1 μg/ml). The cisplatin concentration used was the concentration detected in tumors of treated patients (40 μM or 1 μg/ml). After one hour of cisplatin exposure, the cisplatin was removed and the cultures were grown in the presence of 1 μM of the indicated retinoids for an additional 3 days. The number of living cells present was then determined using the MTS (3-(4,5-dimethylthiazol-2-yl)-5-(3-carboxymethoxyphenyl)-2H-tetrazolium inner salt) assay (Promega). In the MTS assay, metabolically active cells reduce the MTS compound to an aqueous soluble formazan resulting in an absorbance that can be measured at 490 nm (Promega Technical Bulletin No.169). The optical density at 490 nm ($OD_{490}$) of the MTS-treated cultures is then determined and used as a measure of the number of living cells in each well. The percent growth is determined by dividing the $OD_{490}$ of the treated cultures by the $OD_{490}$ of the untreated control cultures.

Figure 2:
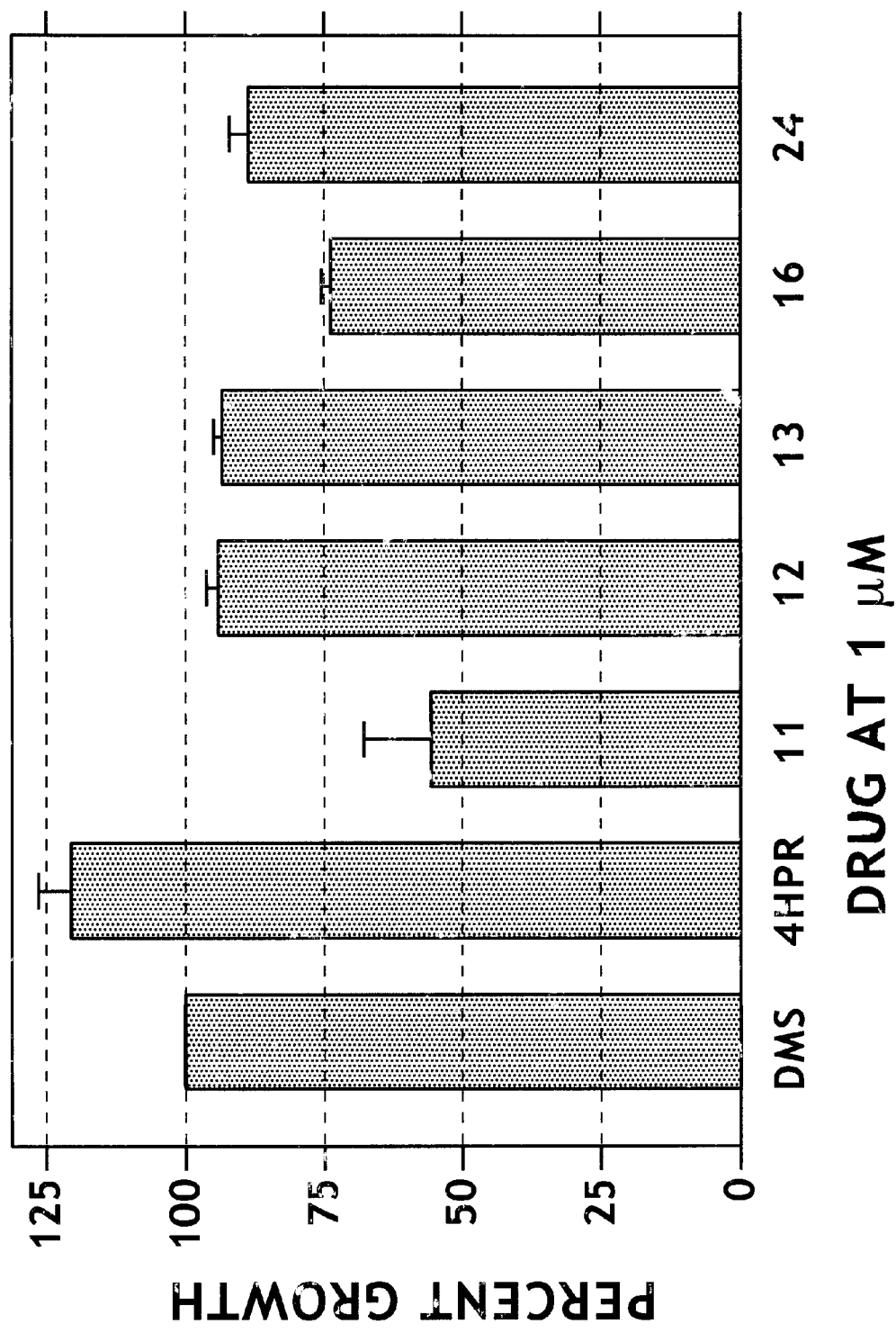
FIG. 2 is a comparison of 1 $\mu$M doses of selected heteroarotinoids with 4-HPR in a cisplatin chemosensitization study.

As indicated in FIG. 2, at a 1 micromolar concentration, the inventive heteroarotinoids, but not 4-HPR are effective. All of the bars in FIG. 2 represent the average and standard deviations of an experiment performed in triplicate. Each bar represents cultures treated with cisplatin in the absence of retinoid (DMSO), or in the presence of 1 μM 4HPR or heteroarotinoids 11, 12, 13, 16 and 24. The culture treated with cisplatin alone (DMSO) is not growth inhibited because OVCAR-3 is a cisplatin-resistant cell line.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A compound selected from those of the isomeric formulas:

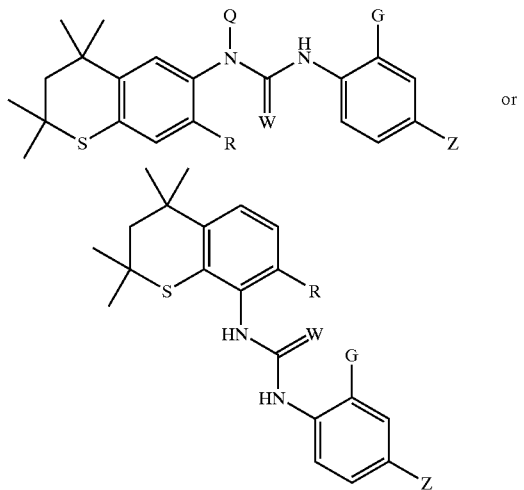

in which:
G denotes H or $CH_3$;
R denotes H, $CH_3$, or $OCH_3$;
Q denotes H or i-$C_3H_7$;
W denotes O or S; and
Z denotes $NO_2$, $CO_2Et$, $CO_2$—n—$C_4H_9$ or $SO_2NH_2$.

2. A compound according to claim 1, wherein:
G=H;
R=H;
Q=H;
W=S; and
Z=$NO_2$.

3. A compound according to claim 1, wherein:
G=H;
R=H;
Q=H;
W=S; and
Z=$CO_2Et$.

4. A compound according to claim 1, wherein:
G=H;
R=H;
Q=H;
W=O; and
Z=$CO_2Et$.

5. A compound according to claim 1, wherein:
G=H;
R=H;
Q=H;
W=O; and
Z=$CO_2H$.

6. A compound according to claim 1, wherein:
G=H;
R=H;
Q=H;
W=S; and
Z=$SO_2NH_2$.

7. A compound according to claim 1, wherein:
G=$CH_3$;
R=H;
Q=H;
W=S; and
Z=$NO_2$.

8. A compound according to claim 1, wherein:
G=H;
R=$CH_3$;
Q=H;
W=S; and
Z=$NO_2$.

9. A compound according to claim 1, wherein:
G=H;
R=$CH_3$;
Q=H;
W=S; and
Z=$CO_2H$.

10. A compound according to claim 1, wherein:
G=$CH_3$;
R=$CH_3$;
Q=H;
W=S; and
Z=$NO_2$.

11. A compound according to claim 1, wherein:
G=H;
R=$CH_3$;
Q=H;
W=S; and
Z=$SO_2NH_2$.

12. A compound according to claim 1, wherein:
G=H;
R=$CH_3$;
Q=H;
W=O; and
Z=$CO_2Et$.

13. The compound according to claim 2, wherein the compound is in the form of the substituted 6-isomer thereof.

14. The compound according to claim 3, wherein the compound is in the form of the substituted 6-isomer thereof.

15. The compound according to claim 4, wherein the compound is in the form of the substituted 6-isomer thereof.

16. A compound selected from those of the isomeric formulas:

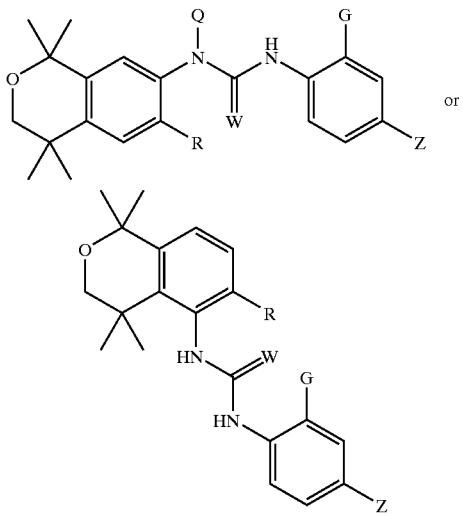

in which:
G denotes H or $CH_3$;
R denotes H, $CH_3$, or $OCH_3$;
Q denotes H or $i$-$C_3H_7$;
W denotes O or S; and
Z denotes $NO_2$, $CO_2Et$, $CO_2$—n—$C_4H_9$ or $SO_2NH_2$.

17. A compound according to claim 16, wherein:
G=H;
R=$OCH_3$;
Q=H;
W=S; and
Z=$NO_2$.

18. A compound according to claim 16, wherein:
G=H;
R=$OCH_3$;
Q=H;
W=S; and
Z=$CO_2Et$.

19. A compound according to claim 16, wherein:
G=H;
R=$OCH_3$;
Q=H;
W=O; and
Z=$CO_2Et$.

20. A compound according to claim 16, wherein:
G=H;
R=$OCH_3$;
Q=H;
W=O; and
Z=$CO_2$—n—Bu.

21. A compound according to claim 16, wherein:
G=$CH_3$;
R=$OCH_3$;
Q=H;
W=S; and
Z=$NO_2$.

22. A compound according to claim 16, wherein:
G=$CH_3$;
R=$OCH_3$;
Q=H;
W=S; and
Z=$SO_2NH_2$.

23. A compound selected from those of the formula:

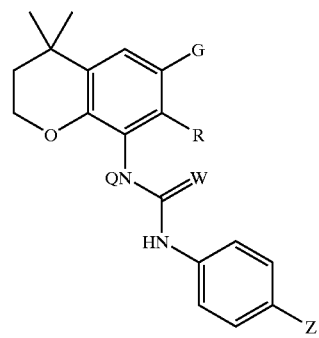

in which:
G denotes H, $CH_3$, C(O)—$CH_3$;
R denotes H, $CH_3$, or $OCH_3$;
W denotes O or S;
Q denotes H or $i$-$C_3H_7$; and
Z denotes $NO_2$, $CO_2Et$ or $CO_2$—n—$C_4H_9$.

24. A method for sensitizing tumor cells in a host to treatment by a chemotherapy agent, comprising administering to the host a tumor sensitizing effective amount of one or more compounds selected from the group consisting of the compounds of claims 1, 16, or 23.

25. A method for treating a tumor bearing host, comprising administering to the host a therapeutically effective amount of one or more compounds selected from the group consisting of the compounds of claims 1, 16 or 23.

26. A method of inhibiting tumor growth or regrowth in a prospective tumor host comprising administering to the host a tumor inhibiting effective amount of one or more compounds selected from the group consisting of the compounds of claims 1, 16 or 23.

27. A pharmaceutical composition, comprising one or more compounds selected from the group consisting of the compounds of claims 1, 16 or 23 in combination with a pharmaceutically acceptable, non-toxic, inert delivery vehicle.

* * * * *